(12) United States Patent
Hollingshead et al.

(10) Patent No.: US 8,808,704 B2
(45) Date of Patent: Aug. 19, 2014

(54) NON-COILED PROTECTIVE REGIONS OF PNEUMOCOCCAL SURFACE PROTEINS PSPA AND PSPC

(75) Inventors: Susan K. Hollingshead, Birmingham, AL (US); David E. Briles, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 1780 days.

(21) Appl. No.: 12/162,566

(22) PCT Filed: Feb. 1, 2007

(86) PCT No.: PCT/US2007/002698
§ 371 (c)(1),
(2), (4) Date: Nov. 26, 2008

(87) PCT Pub. No.: WO2007/089866
PCT Pub. Date: Aug. 9, 2007

(65) Prior Publication Data
US 2009/0170162 A1     Jul. 2, 2009

Related U.S. Application Data

(60) Provisional application No. 60/764,731, filed on Feb. 2, 2006, provisional application No. 60/851,510, filed on Oct. 13, 2006.

(51) Int. Cl.
*A61K 39/09* (2006.01)
*C12N 15/09* (2006.01)

(52) U.S. Cl.
USPC ............... 424/190.1; 424/244.1; 435/69.3

(58) Field of Classification Search
None
See application file for complete search history.

(56) References Cited

U.S. PATENT DOCUMENTS 5,997,882 A * 12/1999 Briles et al. ............... 424/244.1
6,592,876 B1    7/2003 Briles et al.

FOREIGN PATENT DOCUMENTS

WO      WO 97/09994      3/1997
WO      WO9709994    *   3/1997

OTHER PUBLICATIONS

Beall et al 2000 Journal of Clinical Microbiology pp. 3663-3669.*
Greenspan et al. (Nature Biotechnology 7: 936-937, 1999).*
Bowie et al (Science, 1990, 247:1306-1310).*
Swiatlo E. et al., "Oligonucleotides identify conserved and variable regions of pspA and pspA-like sequences of *Streptococcus pneumoniae*" Gene, Elsevier, Amsterdam, NL, vol. 188, No. 2, Apr. 1, 1997, pp. 279-284, X13004059311—ISSN: 0378-1119, * figure 1*.
McDaniel L. S. et al., "Comparison of the PSPA Sequence From *Streptococcus Pneumoniae* EF5668 to the Previously Identified PSPA Sequence From Strain RX1 and Ability of PSPA From EF5668 to Elicit Protection Against Pneumococci of Different Capsular Types" Infection and Immunity, American Society for Microbiology. Washington, vol. 66, No. 10, Oct. 1, 1998, pp. 4748-4754, XP000918186, ISSN: 0019-9567, * figures 2,3 *.
Supplementary European Search Report, mailed May 13, 2009.
International Search Report mailed Dec. 6, 2007.
Beall et al. (J.Clin, Microbiology 2000 vol. 38 pp. 3663-3669), Pneumococcal pspA Sequence Types of Prevalent Multiresistant Pneumococcal Strains in the United States and of Internationally Disseminated Clones.

* cited by examiner

*Primary Examiner* — Padma V Baskar
(74) *Attorney, Agent, or Firm* — Wiley Rein LLP

(57) ABSTRACT

The embodiments described herein provide for immunogenic portions of *Streptococcus pneumoniae* surface protein A and surface protein C lacking alpha helical structure.

5 Claims, 14 Drawing Sheets

FIG. 2A

PspA immunogens as purifed in fusion proteins (and control proteins)

PAC001  283 amino acids

MSDKIIHLTDDSFDTDVLKADGAILVDFWAEWCGPCKMIAPILDEIADEYQGKLTVAKLNIDQNPGTAPKYG
IRGIPTLLLFKNGEVAATKVGALSKGQLKEFLDANLAGSGSGHMHHHHHHSSGLVPRGSGMKETAAAKFERQ
HMDSPDLGTDDDDKAMADLKKAVNEPEKPAEEPENPAPAPAPKPAPAPQPEKPAPAPAPKPEKSADQQAEEDYA
RRSEEYNRLTQQQPPKAEKPAPAPVPKPEQPAPAPKTGWGQENGMWCRQACGRTRAPPPPPLRSGC

FIG. 2B

PAC003  288 amino acids

MSDKIIHLTDDSFDTDVLKADGAILVDFWAEWCGPCKMIAPILDEIADEYQGKLTVAKLNIDQNPGTAPKYG
IRGIPTLLLFKNGEVAATKVGALSKGQLKEFLDANLAGSGSGHMHHHHHHSSGLVPRGSGMKETAAAKFERQ
HMDSPDLGTDDDDKAMADLKKAVNEPETPAPAPAPAPAPAPAPTPEAPAPAPAPKPAPAPAPKPAPAPAPAP
KPAPAPKPAPAPKPAPAPAPKPAEKPAPAPKPETPKTGWKQENGMWCRQACGRTRAPPPPPLRSGC

FIG. 2C

MB001  275 amino acids

MSDKIIHLTDDSFDTDVLKADGAILVDFWAEWCGPCKMIAPILDEIADEYQGKLTVAKLNIDQNPGTAPKYG
IRGIPTLLLFKNGEVAATKVGALSKGQLKEFLDANLAGSGSGHMHHHHHSSGLVPRGSGMKETAAAKFERQ
HMDSPDLGTDDDDKAMAISDPNSLVILEMAKKAELEKTPEKPAEEPENPAPAPQPEKSADQQAEEDYARRSE
EEYNRLTQQPPKAGTNRIRAPSTSLRPHSSTTTTTEIRLLTKPERKLSWLLPPLSNN

FIG. 2D pET32A  189 amino acids_control for

MSDKIIHLTDDSFDTDVLKADGAILVDFWAEWCGPCKMIAPILDEIADEYQGKLTVAKLNIDQNPGTAPKYG
IRGIPTLLLFKNGEVAATKVGALSKGQLKEFLDANLAGSGSGHMHHHHHSSGLVPRGSGMKETAAAKFERQ
HMDSPDLGTDDDDKAMADIGSEFELRRQACGRTRAPPPPLRSGC

FIG. 2E pET32B  185 amino acids

MSDKIIHLTDDSFDTDVLKADGAILVDFWAEWCGPCKMIAPILDEIADEYQGKLTVAKLNIDQNPGTAPKYGI
RGIPTLLLFKNGEVAATKVGALSKGQLKEFLDANLAGSGSGHMHHHHHHSSGLVPRGSGMKETAAAKFERQHM
DSPDLGTDDDDKAMAISDPNSSSVDKLAAALEHHHHHH

FIG. 3A

PspA-specific portion of recombinant protein immunogens

PAC001_pspA  103 amino acids
DLKKAVNEPEKPAEEPENPAPAPAPKPAPAPAPKPAPAPAPKPEKSADQQAEEDYARRSEEE
YNRLTQQQPPKAEKPAPAPVPKPEQPAPAPKTGWGQENGMW

FIG. 3B

PAC003_pspA  107 amino acids
DLKKAVNEPETPAPAPAPAPAPAPAPTPEAPAPAPAPAPAPAPKPAPAPAPKPAPAPAPKPAPAP
KPAPAPKPAPAPAPAPKPEKPAEKPAPAPKPETPKTGWKQENGMW

FIG. 3C

MB001_pspA  77 amino acids
ISDPNSLVILEMAKKAELEKTPEKPAEEPENPAPAPQPEKSADQQAEEDYARRSEEEYNRL
TQQQPPKAGTNRIRA

FIG. 3D

NPB_pspA29 AA
EKSADDQQAEEDYARRSEEEYNRLTQQQP

FIG. 5A

PAC001_pspA      103 Amino Acids

DLKKAVNEPEKPAEEPENPAPAPKPAPAPQPEKPAPAPAPKPEKSADQQAE
EDYARRSEEEYNRLTQQQPPKAEKPAPAPVPKPEQPAPAPKTGWGQENGMW

Chou Fasman 2" structure: Window=7

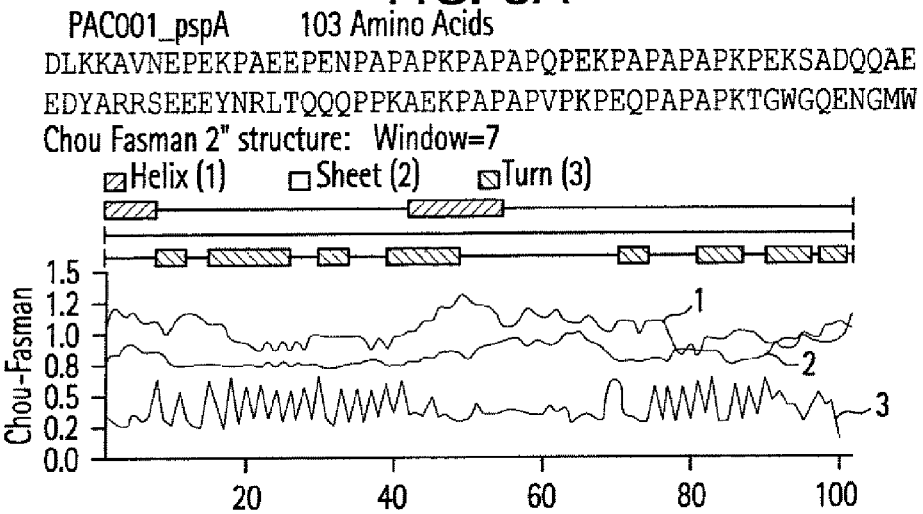

FIG. 5B

PAC003_pspA      107 Amino Acids

DLKKAVNEPETPAPAPAPAPAPAPTPEAPAPAPAPAPKPAPAPKPAPAPK
PAPAPKPAPAPKPAPAPKPAPAPKPAPAPAPAPKPEKPAEKPAPAPKPETPKTGWK
QENGMW

Chou Fasman 2" structure: Window=7

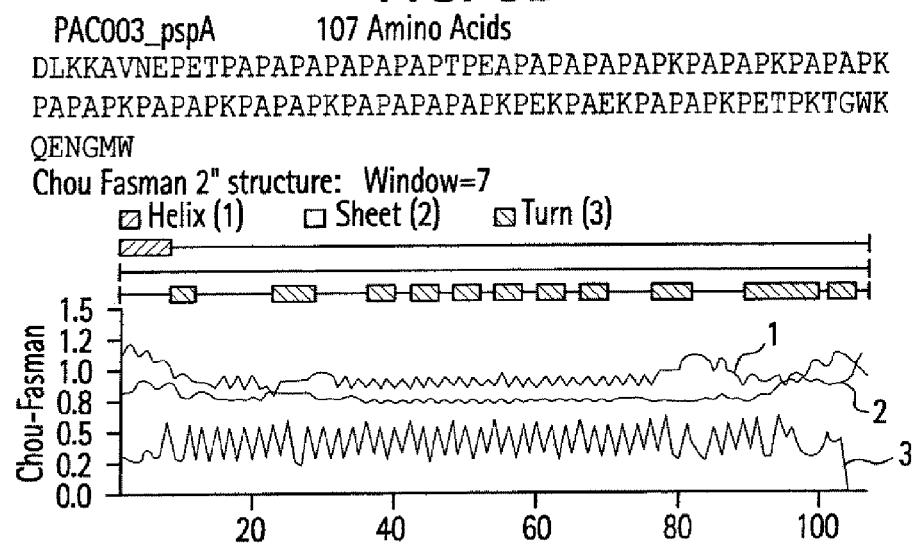

FIG. 5C

MB001_pspA      77 Amino Acids

ISDPNSLVILEMAKKAELEKTPEKPAEEPENPAPAPQPEKSADQQAEEDYARR
SEEEYNRLTQQQPPKAGTNRIRA

Chou Fasman 2" structure: Window=7

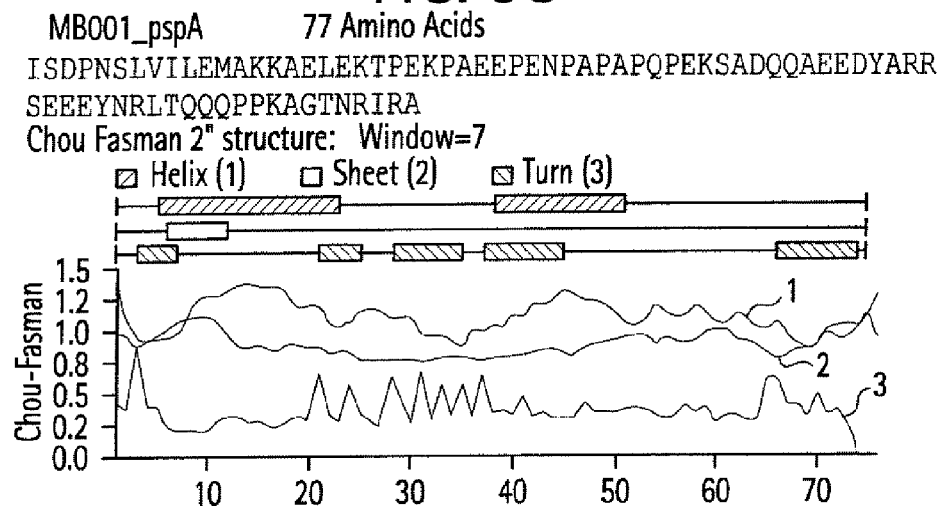

FIG. 6

```
PAC001_pspA.pro  DLKKAVNEPEKPAEEPENPAPAPKPAPAPAPQPEKPAPAPAPAPAPKPEKSADQQA
PAC003_pspA.pro  DLKKAVNEPETPA----PAPAPAPAPTPEAPAPAPAPAPKPAPAPAPAPAPKPAPAPKP
MB001_pspA.pro       ISOPNSLVILEMAKKAELEKTPEKPAEEPENPAPAPQPEKSADQQA
                              *                   *   *     ****.

PAC001_pspA.pro  EEDYARRSEEEYNRLTQQQPPKAEKPAPAPVPKPEQ----PAPAP--------
PAC003_pspA.pro  APAPKPAPAPKPAPAPAPKPAPAPKPAPAPAPKPEKPAEKPAPAPKPETP
MB001_pspA.pro   EEDYARRSEEEYNRLTQQQP--------p--------
                                *

PAC001_pspA.pro  KTGWGQENGMW
PAC003_pspA.pro  KTGWGQENGMW
MB001_pspA.pro   KAGTNRIRA
                 *.*
```

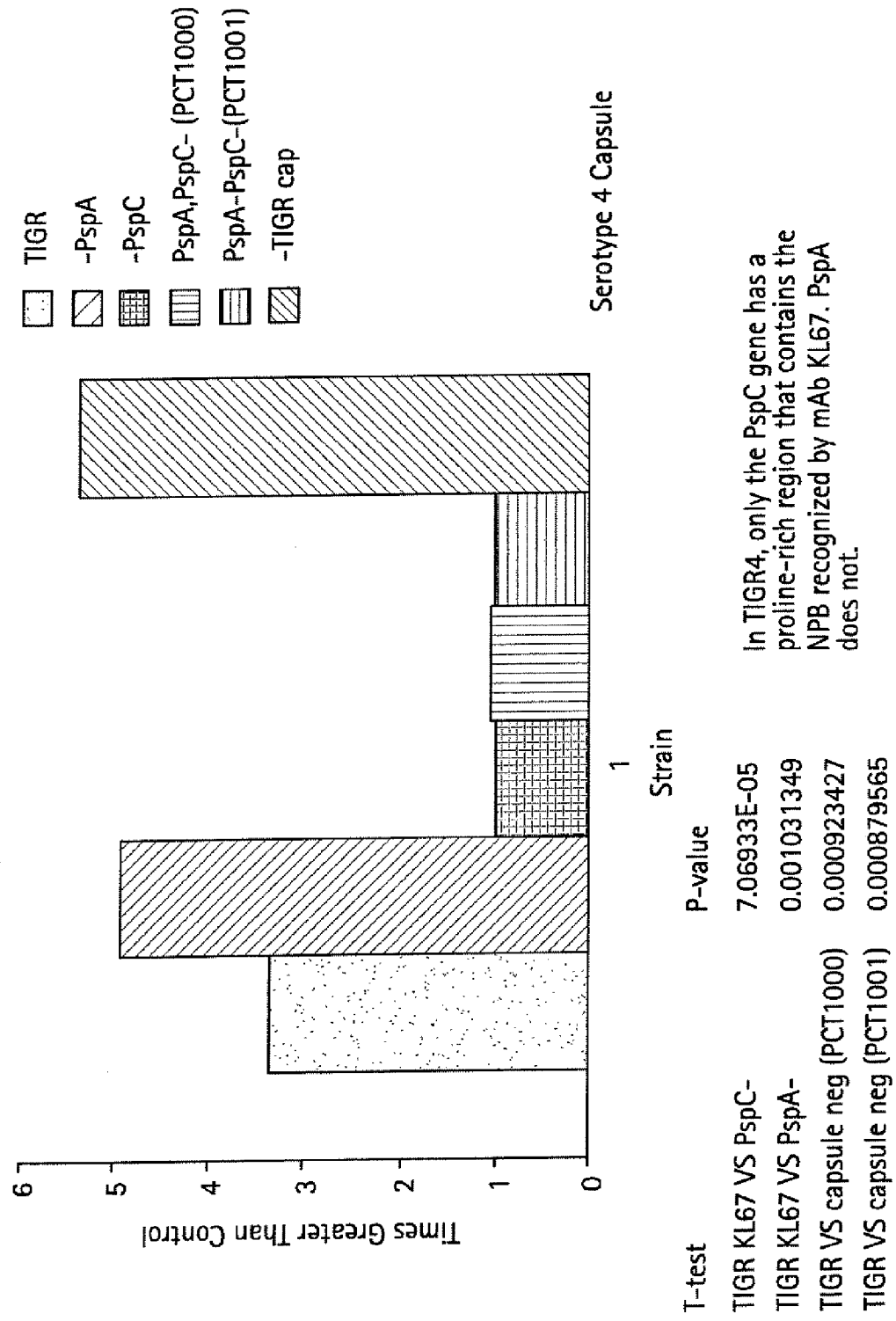

FIG. 12A

Similarity in the sequence of the non-pro-block
in diverse pspA and pspC genes

| | | | |
|---|---|---|---|
| 1_966 | 1 | EKSADQQAEEDYARRSEEEYNRLTQQQP | 28 |
| AMM50525 | 52 | ..TD........................ | 79 |
| CAA05158 | 280 | ..TD........................ | 307 |
| AAF73813 | 346 | ..P......................... | 373 |
| AAF73808 | 300 | ..P......................... | 327 |
| AAF73785 | 440 | ..R......................... | 467 |
| CAA71783 | 284 | ..P.E....................... | 311 |
| AAF73775 | 290 | ..P......................... | 317 |
| AAF73798 | 453 | ..P......................... | 480 |
| AAF73812 | 455 | ..P......................... | 482 |
| AAF73799 | 438 | ..P......................... | 465 |
| AAF73795 | 433 | ..P......................... | 460 |
| AAF73778 | 459 | ..TD........................ | 486 |
| NP_357715 | 363 | ..TD........................ | 390 |
| AAF73776 | 436 | ..P......................... | 463 |
| AAF13456 | 442 | ..TD........................ | 469 |
| AAF73790 | 470 | .NR......................... | 497 |
| NP_359586 | 442 | ..TD........................ | 469 |
| AAC62252 | 408 | ............................ | 435 |
| AAF73810 | 441 | ..P......................... | 468 |
| AAF73777 | 436 | ..P......................... | 463 |
| AAB70838 | 404 | ..TD........................ | 431 |
| AAF73773 | 439 | ..TD........................ | 466 |
| AAF73814 | 439 | ..P......................... | 462 |
| AAF73784 | 461 | ..P......................... | 488 |
| AAF73807 | 474 | ..P......................... | 501 |

FIG. 12B

| ID | Start | Sequence | End |
|---|---|---|---|
| NP_346601 | 474 | ..P........................ | 501 |
| AAF73781 | 447 | ..P........................ | 470 |
| AAF73788 | 439 | ..P........................ | 462 |
| AAF73786 | 441 | ..P.A...................... | 468 |
| AAF73792 | 476 | ..P........................ | 503 |
| AAF27717 | 348 | ....E...................... | 375 |
| AAF27717 | 402 | ....E...................... | 429 |
| ZP_01407806 | 474 | ..P........................ | 501 |
| AAN37736 | 157 | ..P........................ | 184 |
| AAF13458 | 449 | ..P........................ | 476 |
| AAF27708 | 376 | ..P........................ | 403 |
| AAF13455 | 447 | ..P........................ | 474 |
| AAF27701 | 355 | ..P........................ | 382 |
| AAF27719 | 430 | ........................... | 456 |
| AAF68096 | 164 | ........................... | 190 |
| AAF67356 | 188 | ........................... | 214 |
| AAF27716 | 430 | ........................... | 456 |
| AAF68094 | 198 | ........................... | 224 |
| AAF68091 | 151 | ........................... | 177 |
| AAC17445 | 442 | ..TD....................... | 469 |
| AAN37734 | 151 | ..TD....................... | 178 |
| AAF27710 | 369 | ..TD....................... | 396 |
| AAF27704 | 370 | ..TD....................... | 397 |
| AAF68104 | 206 | ..TD....................... | 233 |
| AAF67354 | 199 | ........................... | 224 |
| AAF27698 | 344 | ........................... | 369 |
| AAF27703 | 370 | ..P........D............... | 397 |
| AAF68103 | 166 | ..P........D............... | 193 |
| AAF73822 | 443 | ..PD....................... | 466 |
| AAF73796 | 481 | ........................... | 504 |

SEQUENCE LISTING

```
<160> NUMBER OF SEQ ID NOS: 45

<210> SEQ ID NO 1
<211> LENGTH: 102
<212> TYPE: PRT
<213> ORGANISM: Streptococcus pneumoniae

<400> SEQUENCE: 1

Asp Leu Lys Lys Ala Val Asn Glu Pro Glu Lys Pro Ala Glu Glu Pro
1               5                   10                  15

Glu Asn Pro Ala Pro Ala Pro Lys Pro Ala Pro Ala Pro Gln Pro Glu
            20                  25                  30

Lys Pro Ala Pro Ala Pro Ala Pro Lys Pro Glu Lys Ser Ala Asp Gln
        35                  40                  45

Gln Ala Glu Glu Asp Tyr Ala Arg Arg Ser Glu Glu Glu Tyr Asn Arg
    50                  55                  60

Leu Thr Gln Gln Gln Pro Pro Lys Ala Glu Lys Pro Ala Pro Ala Pro
65                  70                  75                  80

Val Pro Lys Pro Glu Gln Pro Ala Pro Ala Pro Lys Thr Gly Trp Gly
                85                  90                  95

Gln Glu Asn Gly Met Trp
            100

<210> SEQ ID NO 2
<211> LENGTH: 106
<212> TYPE: PRT
<213> ORGANISM: Streptococcus pneumoniae

<400> SEQUENCE: 2
```

Asp Leu Lys Lys Ala Val Asn Glu Pro Glu Thr Pro Ala Pro Ala Pro
1               5                   10                  15

Ala Pro Ala Pro Ala Pro Thr Pro Glu Ala Pro Ala
            20                  25                  30

Pro Ala Pro Ala Pro Lys Pro Ala Pro Ala Pro Lys Pro Ala Pro Ala
            35                  40                  45

Pro Lys Pro Ala Pro Ala Pro Lys Pro Ala Pro Ala Pro Lys Pro Ala
            50                  55                  60

Pro Ala Pro Lys Pro Ala Pro Ala Pro Ala Pro Ala Pro Lys Pro Glu
65                  70                  75                  80

Lys Pro Ala Glu Lys Pro Ala Pro Ala Pro Lys Pro Glu Thr Pro Lys
                85                  90                  95

Thr Gly Trp Lys Gln Glu Asn Gly Met Trp
            100                 105

<210> SEQ ID NO 3
<211> LENGTH: 58
<212> TYPE: PRT
<213> ORGANISM: Artificial
<220> FEATURE:
<223> OTHER INFORMATION: synthetic

<400> SEQUENCE: 3

Met Ala Lys Lys Ala Glu Leu Glu Lys Thr Pro Glu Lys Pro Ala Glu
1               5                   10                  15

Glu Pro Glu Asn Pro Ala Pro Ala Pro Gln Pro Glu Lys Ser Ala Asp
            20                  25                  30

Gln Gln Ala Glu Glu Asp Tyr Ala Arg Arg Ser Glu Glu Tyr Asn
            35                  40                  45

Arg Leu Thr Gln Gln Gln Pro Pro Lys Ala
        50                  55

<210> SEQ ID NO 4
<211> LENGTH: 27
<212> TYPE: PRT
<213> ORGANISM: Streptococcus pneumoniae

<400> SEQUENCE: 4

Glu Lys Ser Ala Asp Gln Gln Ala Glu Glu Asp Tyr Ala Arg Arg Ser
1               5                   10                  15

Glu Glu Glu Tyr Asn Arg Leu Thr Gln Gln Gln
            20                  25

<210> SEQ ID NO 5
<211> LENGTH: 10
<212> TYPE: PRT
<213> ORGANISM: Streptococcus pneumoniae

<400> SEQUENCE: 5

Ala Ala Lys Lys Ala Glu Leu Glu Lys Thr
1               5                   10

<210> SEQ ID NO 6
<211> LENGTH: 28
<212> TYPE: PRT
<213> ORGANISM: Streptococcus pneumoniae

<400> SEQUENCE: 6

Met Glu Lys Ser Ala Asp Gln Gln Ala Glu Glu Asp Tyr Ala Arg Arg
1               5                   10                  15

Ser Glu Glu Glu Tyr Asn Arg Leu Thr Gln Gln Gln
            20                  25

<210> SEQ ID NO 7
<211> LENGTH: 28
<212> TYPE: PRT
<213> ORGANISM: Streptococcus pneumoniae

<400> SEQUENCE: 7

Met Glu Lys Ser Val Asp Gln Gln Ala Glu Glu Asp Tyr Ala Arg Arg
1               5                   10                  15

Ser Glu Glu Glu Tyr Asn Arg Leu Thr Gln Gln Gln
            20                  25

<210> SEQ ID NO 8
<211> LENGTH: 8
<212> TYPE: PRT
<213> ORGANISM: Streptococcus pneumoniae

<400> SEQUENCE: 8

Asp Leu Lys Lys Ala Val Asn Glu
1               5

<210> SEQ ID NO 9
<211> LENGTH: 11
<212> TYPE: PRT
<213> ORGANISM: Streptococcus pneumoniae
<220> FEATURE:
<221> NAME/KEY: MISC_FEATURE
<222> LOCATION: (1)..(1)
<223> OTHER INFORMATION: can be Lys or Gly
<220> FEATURE:
<221> NAME/KEY: MISC_FEATURE
<222> LOCATION: (5)..(5)
<223> OTHER INFORMATION: can be Lys or Gly

<400> SEQUENCE: 9

Xaa Thr Gly Trp Xaa Gln Glu Asn Gly Met Trp
1               5                   10

<210> SEQ ID NO 10
<211> LENGTH: 306
<212> TYPE: DNA
<213> ORGANISM: Streptococcus pneumoniae

<400> SEQUENCE: 10
gaccttaaga aagcagttaa tgagccagaa aaaccagctg aagagcctga gaatccagct      60
cctgcaccaa aaccagcgcc ggctcctcaa ccagaaaaac cagctccagc tcctgcacca     120
aaaccagaga agtcagcaga tcaacaagct gaagaagact atgctcgtag atcagaagaa     180
gaatataacc gcttgactca acagcaaccg ccaaaagcag aaaaaccagc tccagctcct     240
gtaccaaaac cagagcaacc agctcccgca ccaaaaacgg gctggggaca agaaaacggt     300
atgtgg                                                                306

<210> SEQ ID NO 11
<211> LENGTH: 318
<212> TYPE: DNA
<213> ORGANISM: Streptococcus pneumoniae

<400> SEQUENCE: 11
gaccttaaga aagcagttaa tgagccagaa actccagctc cggctccagc cccagctcca      60
gctccagctc caactccaga agccccagct ccagctccag ctccggctcc taaaccagct     120

```
ccggctccta aaccagctcc ggctcctaaa ccagctccgg ctcctaaacc agctccggct    180
cctaaaccag ctccggctcc taaaccagct ccagctccag ctccggctcc taaaccagaa    240
aagccagcag aaaaaccagc tccagctcct aaaccagaaa ctccaaaaac aggctggaaa    300
caagaaaacg gtatgtgg                                                  318
```

```
<210> SEQ ID NO 12
<211> LENGTH: 174
<212> TYPE: DNA
<213> ORGANISM: Streptococcus pneumoniae

<400> SEQUENCE: 12
atggctaaaa aagctgaatt agaaaaaact ccagaaaaac cagctgaaga gcctgagaat    60
ccagctccag caccacaacc agagaagtca gcagatcaac aagctgaaga agactatgct   120
cgtagatcag aagaagaata taatcgcttg acccaacagc aaccgccaaa agca         174
```

```
<210> SEQ ID NO 13
<211> LENGTH: 84
<212> TYPE: DNA
<213> ORGANISM: Streptococcus pneumoniae

<400> SEQUENCE: 13
gagaagtcag cagatcaaca agctgaagaa gactatgctc gtagatcaga agaagaatat    60
aatcgcttga cccaacagca accg                                           84
```

```
<210> SEQ ID NO 14
<211> LENGTH: 84
<212> TYPE: DNA
<213> ORGANISM: Streptococcus pneumoniae

<400> SEQUENCE: 14
gagaagtcag cagatcaaca agctgaagaa gactatgctc gtagatcaga agaagaatat    60
aaccgcttga ctcaacagca accg                                           84
```

```
<210> SEQ ID NO 15
<211> LENGTH: 23
<212> TYPE: PRT
<213> ORGANISM: Streptococcus pneumoniae

<400> SEQUENCE: 15

Asp Gln Gln Ala Glu Glu Asp Tyr Ala Arg Arg Ser Glu Glu Glu Tyr
1               5                   10                  15

Asn Arg Leu Thr Gln Gln Gln
            20
```

```
<210> SEQ ID NO 16
<211> LENGTH: 40
<212> TYPE: DNA
<213> ORGANISM: Streptococcus pneumoniae

<400> SEQUENCE: 16
gggagccatg gctgacctta agaaagcagt taatgagcca                          40
```

```
<210> SEQ ID NO 17
<211> LENGTH: 36
<212> TYPE: DNA
<213> ORGANISM: Streptococcus pneumoniae

<400> SEQUENCE: 17
```
ccgtcgacac cacataccgt tttcttgttt ccagcc          36

<210> SEQ ID NO 18
<211> LENGTH: 283
<212> TYPE: PRT
<213> ORGANISM: Streptococcus pneumoniae

<400> SEQUENCE: 18

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Asp Leu Lys Lys Ala Val Asn Glu Pro Glu Lys Pro Ala Glu Glu
                165                 170                 175

Pro Glu Asn Pro Ala Pro Ala Pro Lys Pro Ala Pro Ala Pro Gln Pro
            180                 185                 190

Glu Lys Pro Ala Pro Ala Pro Ala Pro Lys Pro Glu Lys Ser Ala Asp
        195                 200                 205

Gln Gln Ala Glu Glu Asp Tyr Ala Arg Arg Ser Glu Glu Glu Tyr Asn
    210                 215                 220

Arg Leu Thr Gln Gln Gln Pro Pro Lys Ala Glu Lys Pro Ala Pro Ala
225                 230                 235                 240

Pro Val Pro Lys Pro Glu Gln Pro Ala Pro Ala Pro Lys Thr Gly Trp
                245                 250                 255

Gly Gln Glu Asn Gly Met Trp Cys Arg Gln Ala Cys Gly Arg Thr Arg
            260                 265                 270

Ala Pro Pro Pro Pro Pro Leu Arg Ser Gly Cys
        275                 280

<210> SEQ ID NO 19
<211> LENGTH: 327
<212> TYPE: DNA
<213> ORGANISM: Streptococcus pneumoniae
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (325)..(327)
<223> OTHER INFORMATION: n is a, c, g, or t

<400> SEQUENCE: 19

```
nnnccatggc tgaccttaag aaagcagtta atgagccaga aaaaccagct gaagagcctg    60
agaatccagc tcctgcacca aaaccagcgc cggctcctca accagaaaaa ccagctccag   120
ctcctgcacc aaaaccagag aagtcagcag atcaacaagc tgaagaagac tatgctcgta   180
gatcagaaga agaatataac cgcttgactc aacagcaacc gccaaaagca gaaaaaccag   240
ctccagctcc tgtaccaaaa ccagagcaac cagctcccgc accaaaaacg ggctggggac   300
aagaaaacgg tatgtggtgt cgacnnn                                       327
```

<210> SEQ ID NO 20
<211> LENGTH: 286
<212> TYPE: PRT
<213> ORGANISM: Streptococcus pneumoniae

<400> SEQUENCE: 20

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Met His His His His His His Ser Ser Gly Leu Val Pro
            115                 120                 125

Arg Gly Ser Gly Met Lys Glu Thr Ala Ala Ala Lys Phe Glu Arg Gln
        130                 135                 140

His Met Asp Ser Pro Asp Leu Gly Thr Asp Asp Asp Asp Lys Ala Met
145                 150                 155                 160

Ala Asp Leu Lys Lys Ala Val Asn Glu Pro Glu Thr Pro Ala Pro Ala
                165                 170                 175

Pro Ala Pro Ala Pro Ala Pro Thr Pro Glu Ala Pro Ala Pro
            180                 185                 190

Ala Pro Ala Pro Ala Pro Lys Pro Ala Pro Ala Pro Lys Pro Ala Pro
        195                 200                 205

Ala Pro Lys Pro Ala Pro Ala Pro Lys Pro Ala Pro Ala Pro Lys Pro
    210                 215                 220

Ala Pro Ala Pro Lys Pro Ala Pro Ala Pro Ala Pro Lys Pro
225                 230                 235                 240

Glu Lys Pro Ala Glu Lys Pro Ala Pro Ala Pro Lys Pro Glu Thr Pro
                245                 250                 255

Lys Thr Gly Trp Lys Gln Glu Asn Gly Met Trp Cys Arg Gln Ala Cys
            260                 265                 270

Gly Arg Thr Arg Ala Pro Pro Pro Pro Leu Arg Ser Gly
        275                 280                 285
```

<210> SEQ ID NO 21
<211> LENGTH: 338
<212> TYPE: DNA

```
<213> ORGANISM: Streptococcus pneumoniae
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (336)..(338)
<223> OTHER INFORMATION: n is a, c, g, or t

<400> SEQUENCE: 21
nnncatggct gaccttaaga aagcagttaa tgagccagaa actccagctc cggctccagc      60
cccagctcca gctccagctc caactccaga agccccagct ccagctccag ctccggctcc     120
taaaccagct ccggctccta accagctccc ggctcctaaa ccagctccgg ctcctaaacc     180
agctccggct cctaaaccag ctccggctcc taaaccagct ccagctccag ctccggctcc     240
taaaccagaa aagccagcag aaaaaccagc tccagctcct aaaccagaaa ctccaaaaac     300
aggctggaaa caagaaaacg gtatgtggtg tcgacnnn                             338

<210> SEQ ID NO 22
<211> LENGTH: 9
<212> TYPE: PRT
<213> ORGANISM: Streptococcus pneumoniae

<400> SEQUENCE: 22

Ala Lys Lys Ala Glu Leu Glu Lys Ala
1               5

<210> SEQ ID NO 23
<211> LENGTH: 9
<212> TYPE: PRT
<213> ORGANISM: Streptococcus pneumoniae

<400> SEQUENCE: 23

Ala Lys Lys Ala Glu Leu Glu Lys Thr
1               5

<210> SEQ ID NO 24
<211> LENGTH: 9
<212> TYPE: PRT
<213> ORGANISM: Streptococcus pneumoniae

<400> SEQUENCE: 24

Thr Lys Lys Ala Glu Leu Glu Lys Thr
1               5

<210> SEQ ID NO 25
<211> LENGTH: 9
<212> TYPE: PRT
<213> ORGANISM: Streptococcus pneumoniae

<400> SEQUENCE: 25

Thr Lys Lys Ala Glu Leu Glu Lys Thr
1               5

<210> SEQ ID NO 26
<211> LENGTH: 20
<212> TYPE: PRT
<213> ORGANISM: Streptococcus pneumoniae

<400> SEQUENCE: 26

Pro Glu Lys Pro Ala Glu Glu Pro Glu Asn Pro Ala Pro Ala Pro Gln
1               5                   10                  15
```

Pro Glu Lys Ser
            20

<210> SEQ ID NO 27
<211> LENGTH: 5
<212> TYPE: PRT
<213> ORGANISM: Streptococcus pneumoniae

<400> SEQUENCE: 27

Pro Ala Pro Ala Pro
1               5

<210> SEQ ID NO 28
<211> LENGTH: 5
<212> TYPE: PRT
<213> ORGANISM: Streptococcus pneumoniae

<400> SEQUENCE: 28

Pro Glu Lys Pro Ala
1               5

<210> SEQ ID NO 29
<211> LENGTH: 24
<212> TYPE: DNA
<213> ORGANISM: Streptococcus pneumoniae

<400> SEQUENCE: 29
ggtacctgct tttggcggtt gctg                                           24

<210> SEQ ID NO 30
<211> LENGTH: 162
<212> TYPE: DNA
<213> ORGANISM: Streptococcus pneumoniae

<400> SEQUENCE: 30
ctcgagatgg ctaaaaaagc tgaattagaa aaaactccag aaaaaccagc tgaagagcct      60
gagaatccag cttcagcacc acaaccacaa caagctgaag aagactatgc tcgtagatca     120
gaagaagaat ataatcgctt gacccaagca ggaaaaacca gc                        162

<210> SEQ ID NO 31
<211> LENGTH: 212
<212> TYPE: DNA
<213> ORGANISM: Streptococcus pneumoniae

<400> SEQUENCE: 31
gaattcacta gtgattctcg agatggctaa aaaagctgaa ttagaaaaaa ctccagaaaa      60
accagctgaa gagcctgaga atccagctcc agcaccacaa ccagagaagt cagcagatca     120
acaagctgaa gaagactatg ctcgtagatc agaagaagaa tataatcgct tgacccaaca     180
gcaaccgcca aaagcaggta ccaatcgaat tc                                   212

<210> SEQ ID NO 32
<211> LENGTH: 274
<212> TYPE: PRT
<213> ORGANISM: Artificial
<220> FEATURE:
<223> OTHER INFORMATION: synthetic

<400> SEQUENCE: 32

Met Ser Asp Lys His His Leu Thr Asp Asp Ser Phe Asp Thr Asp Val
1               5                   10                  15

Leu Lys Ala Asp Gly Ala Ile Leu Val Asp Phe Trp Ala Glu Trp Cys

```
            20                  25                  30
Gly Pro Cys Lys Met Ile Ala Pro Ile Leu Asp Glu Ile Ala Asp Glu
            35                  40                  45

Tyr Gln Gly Lys Leu Thr Val Ala Lys Leu Asn Ile Asp Gln Asn Pro
 50                  55                  60

Gly Thr Ala Pro Lys Tyr Gly Ile Arg Gly Ile Pro Thr Leu Leu Leu
 65                  70                  75                  80

Phe Lys Asn Gly Glu Val Ala Thr Lys Val Gly Ala Leu Ser Lys
                 85                  90                  95

Gly Gln Leu Lys Glu Phe Leu Asp Ala Asn Leu Ala Gly Ser Gly Ser
            100                 105                 110

Gly His Met His His His His His His Ser Ser Gly Leu Val Pro Arg
            115                 120                 125

Gly Ser Gly Met Lys Glu Thr Ala Ala Ala Lys Phe Glu Arg Gln His
            130                 135                 140

Met Asp Ser Pro Asp Leu Gly Thr Asp Asp Asp Lys Ala Met Ala
145                 150                 155                 160

Ile Ser Asp Pro Asn Ser Leu Val Ile Leu Glu Met Ala Lys Lys Ala
                165                 170                 175

Glu Leu Glu Lys Thr Pro Glu Lys Pro Ala Glu Pro Glu Asn Pro
                180                 185                 190

Ala Pro Ala Pro Gln Pro Glu Lys Ser Ala Asp Gln Ala Glu Glu
            195                 200                 205

Asp Tyr Ala Arg Arg Ser Glu Glu Tyr Asn Arg Leu Thr Gln Gln
            210                 215                 220

Gln Pro Pro Lys Ala Gly Thr Asn Arg Ile Arg Ala Pro Ser Thr Ser
225                 230                 235                 240

Leu Arg Pro His Ser Ser Thr Thr Thr Thr Thr Glu Ile Arg Leu
                245                 250                 255

Leu Thr Lys Pro Glu Arg Lys Leu Ser Trp Leu Leu Pro Pro Leu Ser
                260                 265                 270

Asn Asn

<210> SEQ ID NO 33
<211> LENGTH: 33
<212> TYPE: DNA
<213> ORGANISM: Streptococcus pneumoniae

<400> SEQUENCE: 33
gacgacgaca agatggagaa gtcagcagat caa                              33

<210> SEQ ID NO 34
<211> LENGTH: 39
<212> TYPE: DNA
<213> ORGANISM: Streptococcus pneumoniae

<400> SEQUENCE: 34
gaggagaagc ccggtttacc gttgctgttg agtcaagcg                        39

<210> SEQ ID NO 35
<211> LENGTH: 306
<212> TYPE: PRT
<213> ORGANISM: Artificial
<220> FEATURE:
<223> OTHER INFORMATION: synthetic

<400> SEQUENCE: 35
```

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Gly Ser Thr Ser
210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Lys Phe Glu
            245                 250                 255

Arg Gln His Met Asp Ser Pro Asp Leu Gly Thr Gly Gly Ser Gly
            260                 265                 270

Asp Asp Asp Asp Lys Met Glu Lys Ser Ala Asp Gln Gln Ala Glu Glu
            275                 280                 285

Asp Tyr Ala Arg Arg Ser Glu Glu Tyr Asn Arg Leu Thr Gln Gln
290                 295                 300

Gln Pro
305

<210> SEQ ID NO 36
<211> LENGTH: 117
<212> TYPE: DNA
<213> ORGANISM: Streptococcus pneumoniae

<400> SEQUENCE: 36
gacgacgaca agatggagaa gtcagcagat caacaagctg aagaagacta tgctcgtaga      60
tcagaagaag aatataatcg cttgacccaa cagcaaccgt aaaccgggct tctcctc       117

<210> SEQ ID NO 37
<211> LENGTH: 33
<212> TYPE: DNA
<213> ORGANISM: Streptococcus pneumoniae

<400> SEQUENCE: 37
```
gacgacgaca agatggagaa gtcagcagat caa          33

<210> SEQ ID NO 38
<211> LENGTH: 39
<212> TYPE: DNA
<213> ORGANISM: Streptococcus pneumoniae

<400> SEQUENCE: 38
gaggagaagc ccggtttacc gttgctgttg agtcaagcg    39

<210> SEQ ID NO 39
<211> LENGTH: 306
<212> TYPE: PRT
<213> ORGANISM: Streptococcus pneumoniae

<400> SEQUENCE: 39

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Met Glu Lys Ser Ala Asp Gln Ala Glu Glu
        275                 280                 285

Asp Tyr Ala Arg Arg Ser Glu Glu Glu Tyr Asn Arg Leu Thr Gln Gln
    290                 295                 300

Gln Pro

<210> SEQ ID NO 40
<211> LENGTH: 117
<212> TYPE: DNA
<213> ORGANISM: Streptococcus pneumoniae

<400> SEQUENCE: 40
gacgacgaca agatggagaa gtcagcagat caacaagctg aagaagacta tgctcgtaga       60
tcagaagaag aatataatcg cttgacccaa cagcaaccgt aaaccgggct tctcctc        117

<210> SEQ ID NO 41
<211> LENGTH: 275
<212> TYPE: PRT
<213> ORGANISM: Artificial
<220> FEATURE:
<223> OTHER INFORMATION: synthetic

<400> SEQUENCE: 41

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
        115                 120                 125

Arg Gly Ser Gly Met Lys Glu Thr Ala Ala Ala Lys Phe Glu Arg Gln
130                 135                 140

His Met Asp Ser Pro Asp Leu Gly Thr Asp Asp Asp Lys Ala Met
145                 150                 155                 160

Ala Ile Ser Asp Pro Asn Ser Leu Val Ile Leu Glu Met Ala Lys Lys
                165                 170                 175

Ala Glu Leu Glu Lys Thr Pro Glu Lys Pro Ala Glu Glu Pro Glu Asn
            180                 185                 190

Pro Ala Pro Ala Pro Gln Pro Glu Lys Ser Ala Asp Gln Gln Ala Glu
        195                 200                 205

Glu Asp Tyr Ala Arg Arg Ser Glu Glu Glu Tyr Asn Arg Leu Thr Gln
    210                 215                 220

Gln Gln Pro Pro Lys Ala Gly Thr Asn Arg Ile Arg Ala Pro Ser Thr
225                 230                 235                 240

Ser Leu Arg Pro His Ser Ser Thr Thr Thr Thr Thr Glu Ile Arg
                245                 250                 255

Leu Leu Thr Lys Pro Glu Arg Lys Leu Ser Trp Leu Leu Pro Pro Leu
            260                 265                 270

Ser Asn Asn
        275

<210> SEQ ID NO 42
<211> LENGTH: 189
<212> TYPE: PRT
<213> ORGANISM: Artificial
<220> FEATURE:
<223> OTHER INFORMATION: synthetic

<400> SEQUENCE: 42

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
        115                 120                 125

Arg Gly Ser Gly Met Lys Glu Thr Ala Ala Ala Lys Phe Glu Arg Gln
130                 135                 140

His Met Asp Ser Pro Asp Leu Gly Thr Asp Asp Asp Asp Lys Ala Met
145                 150                 155                 160

Ala Asp Ile Gly Ser Glu Phe Glu Leu Arg Arg Gln Ala Cys Gly Arg
                165                 170                 175

Thr Arg Ala Pro Pro Pro Pro Leu Arg Ser Gly Cys
            180                 185

<210> SEQ ID NO 43
<211> LENGTH: 184
<212> TYPE: PRT
<213> ORGANISM: Artificial
<220> FEATURE:
<223> OTHER INFORMATION: synthetic

<400> SEQUENCE: 43

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
        115                 120                 125

```
Arg Gly Ser Gly Met Lys Glu Thr Ala Ala Ala Lys Phe Glu Arg Gln
        130                 135                 140

His Met Asp Ser Pro Asp Leu Gly Thr Asp Asp Asp Lys Ala Met
145                 150                 155                 160

Ala Ile Ser Asp Pro Asn Ser Ser Ser Val Asp Lys Leu Ala Ala Ala
                    165                 170                 175

Leu Glu His His His His His His
            180

<210> SEQ ID NO 44
<211> LENGTH: 76
<212> TYPE: PRT
<213> ORGANISM: Streptococcus pneumoniae

<400> SEQUENCE: 44

Ile Ser Asp Pro Asn Ser Leu Val Ile Leu Glu Met Ala Lys Lys Ala
1               5                   10                  15

Glu Leu Glu Lys Thr Pro Glu Lys Pro Ala Glu Pro Glu Asn Pro
            20                  25                  30

Ala Pro Ala Pro Gln Pro Glu Lys Ser Ala Asp Gln Gln Ala Glu Glu
            35                  40                  45

Asp Tyr Ala Arg Arg Ser Glu Glu Tyr Asn Arg Leu Thr Gln Gln
        50                  55                  60

Gln Pro Pro Lys Ala Gly Thr Asn Arg Ile Arg Ala
65                  70                  75

<210> SEQ ID NO 45
<211> LENGTH: 28
<212> TYPE: PRT
<213> ORGANISM: Streptococcus pneumoniae

<400> SEQUENCE: 45

Glu Lys Ser Ala Asp Gln Gln Ala Glu Glu Asp Tyr Ala Arg Arg Ser
1               5                   10                  15

Glu Glu Glu Tyr Asn Arg Leu Thr Gln Gln Gln Pro
            20                  25
```

US 8,808,704 B2

NON-COILED PROTECTIVE REGIONS OF PNEUMOCOCCAL SURFACE PROTEINS PSPA AND PSPC

FEDERAL FUNDING

This invention was funded, in part, by the Federal Government under NIH/NIAID Contract No. R01 AI21543. Accordingly, the Federal Government may have certain rights in this invention.

FIELD OF THE INVENTION

The embodiments described herein relate to molecular immunology, bacteriology, and vaccine development. More specifically, the various embodiments relate to antigenic and immunogenic portions of *Streptococcus pneumoniae* surface protein A and surface protein C that lack alpha-helical structure.

BACKGROUND OF THE INVENTION

*Streptococcus pneumoniae* is a well known human pathogen and a major etiologic agent for pneumonia, meningitis, otitis media as well as sepsis, among primarily young children and older adults. Antibodies to a capsular polysaccharide (PS) may provide protection against pneumococci expressing the same capsular serotype. Currently available pneumococcal vaccines contain a mixture of capsular PS of multiple serotypes. For example, one pneumococcal vaccine contains capsular PS from twenty-three commonly found serotypes. The most recently developed type of vaccine contains capsular PS from seven to thirteen serotypes that are conjugated to a protein molecule. A seven-valent conjugate vaccine was introduced in 2000 for clinical use in the USA, and has reduced the incidence of invasive pneumococcal diseases in children and in adults.

An alternative approach for protecting children and the elderly from pneumococcal infection employs protein antigens that could elicit protective immune responses. Such proteins may serve as a vaccine by themselves, may be used in conjunction with successful polysaccharide-protein conjugates, or serve as carriers for polysaccharide components. The pneumococcal surface protein A (PspA) has been identified as an immunogenic protein with potential for pneumococcal vaccines.

Most of the work concerning PspA as a potential for a protein-based pneumococcal vaccine has focused on cross-protective epitopes lying within the alpha-helical region of the PspA protein, a region predicted to have a coiled-coil protein conformation. It has been suggested, however, that this alpha-helical region may have the potential to elicit antibodies that cross-react with proteins of the human heart and skeletal muscles. On the other hand, adults often have PspA antibodies, naturally elicited during childhood, that have no connection to rheumatic heart disease or auto-reactive immune syndromes. Nevertheless, there remains a need for pneumococcal surface polypeptides that are immunogenic yet minimize risk of self-reactive responses.

SUMMARY OF THE INVENTION

Embodiments described herein provide for non-alpha-helical regions of PspA and PspC polypeptides that are capable of eliciting an immune response. In some embodiments, these polypeptides, when used as a component of a vaccine, provide protective immunity against pneumococcal disease.

In other embodiments, the polypeptides have the amino acid sequence DLKKAVNEPEKPAEEPENPAPAPKPAPA-PQPEKPAPAPAPKPEKSADQQAEEDYARR SEEEYNR-LTQQQPPKAEKPAPAPVPKPEQPAPAPK-TGWGQENGMW [SEQ ID NO: 1]; DLKKAVNEPETPAPAPAPAPAPTPEA-PAPAPAPAPKPAPAPKPAPAPKPAPAPKPA PAPKPAPA-PKPAPAPAPAPKPEKPAEKPAPAPKPET-PKTGWKQENGMW [SEQ ID NO: 2]; MAKKAELEKTPEKPAEEPENPAPAPQ-PEKSADQQAEEDYARRSEEEYNRLTQQQPPK A [SEQ ID NO: 3]; or EKSADQQAEEDYARRSEEEYNRLTQQQ [SEQ ID NO: 4], and antigenic or immunogenic homologs, portions, fragments, variants, or derivatives of any of the foregoing.

Another aspect of the invention provides for a vaccine comprising the non-alpha-helical regions of PspA and PspC polypeptides. In other aspects, the vaccine may include one or more of the peptides with the amino acid sequences designated in SEQ ID NO: 1, SEQ ID NO: 2, SEQ ID NO: 3 or SEQ ID NO: 4 and antigenic or immunogenic homologs, portions, fragments, variants, or derivatives thereof.

Another embodiment provides for nucleic acids encoding the immunogenic non-alpha-helical regions of PspA and PspC polypeptides, vector comprising these nucleic acids, and host cells comprising these nucleic acids or vectors. Another embodiment provides for host cells that produce the immunogenic non-alpha-helical regions of PspA and PspC polypeptides.

A further aspect provides for a method of making an immunogenic polypeptide constituting a non-alpha-helical region of a PspA or PspC polypeptide comprising the step of preparing the polypeptide from a host cell that expresses the polypeptide.

Another aspect provides for a method of immunizing a patient comprising administering an effective amount of at least one immunogenic polypeptide constituting a non-alpha-helical region of a PspA or PspC polypeptide.

BRIEF DESCRIPTION OF THE DRAWINGS

FIGS. 2A-2E present the amino acid sequences of recombinant PspA polypeptides. FIG. 2A: PAC001 (SEQ ID NO:18); FIG. 2B: PAC003 (SEQ ID NO:20); FIG. 2C: MB001 (SEQ ID NO:41); FIG. 2D: PET32A (SEQ ID NO:42); FIG. 2E: PET32B (SEQ ID NO:43).

FIGS. 3A-D present PspA-specific portions of embodiments of recombinant protein immunogens. FIG. 3A: PAC001_pspA (SEQ ID NO:1); FIG. 3B: PAC003_pspA (SEQ ID NO:2); FIG. 3C: MB001_pspA (SEQ ID NO:44); FIG. 3D: NPB_pspA29 AA (SEQ ID NO:45).

FIGS. 5A-C present Chou-Fasman structural probability plots of the PspA-specific immunogenic polypeptides. FIG. 5A: PAC001_pspA (SEQ ID NO:1); FIG. 5B: PAC003_pspA (SEQ ID NO:2); FIG. 5C: MB001_pspA (SEQ ID NO:44).

FIG. 6 shows the alignment of example embodiments of immunogenic PspA/PspC polypeptides. PAC001_pspA.pro (SEQ ID NO:1); PAC003_pspA.pro (SEQ ID NO:2); MB001_pspA.pro (SEQ ID NO:44).

FIG. 11 presents data from FACS binding of mAb KL67 to TIGR4 wild-type strain and mutant strains that lack capsule, PspA, PspC, or both PspA and PspC.

FIGS. 12A-B indicate the similarity in the sequence of the non-pro-block in the diverse pspA and pspC genes; as compared to 1_966 (SEQ ID NO:45).

DETAILED DESCRIPTION OF THE INVENTION

Figure 1:
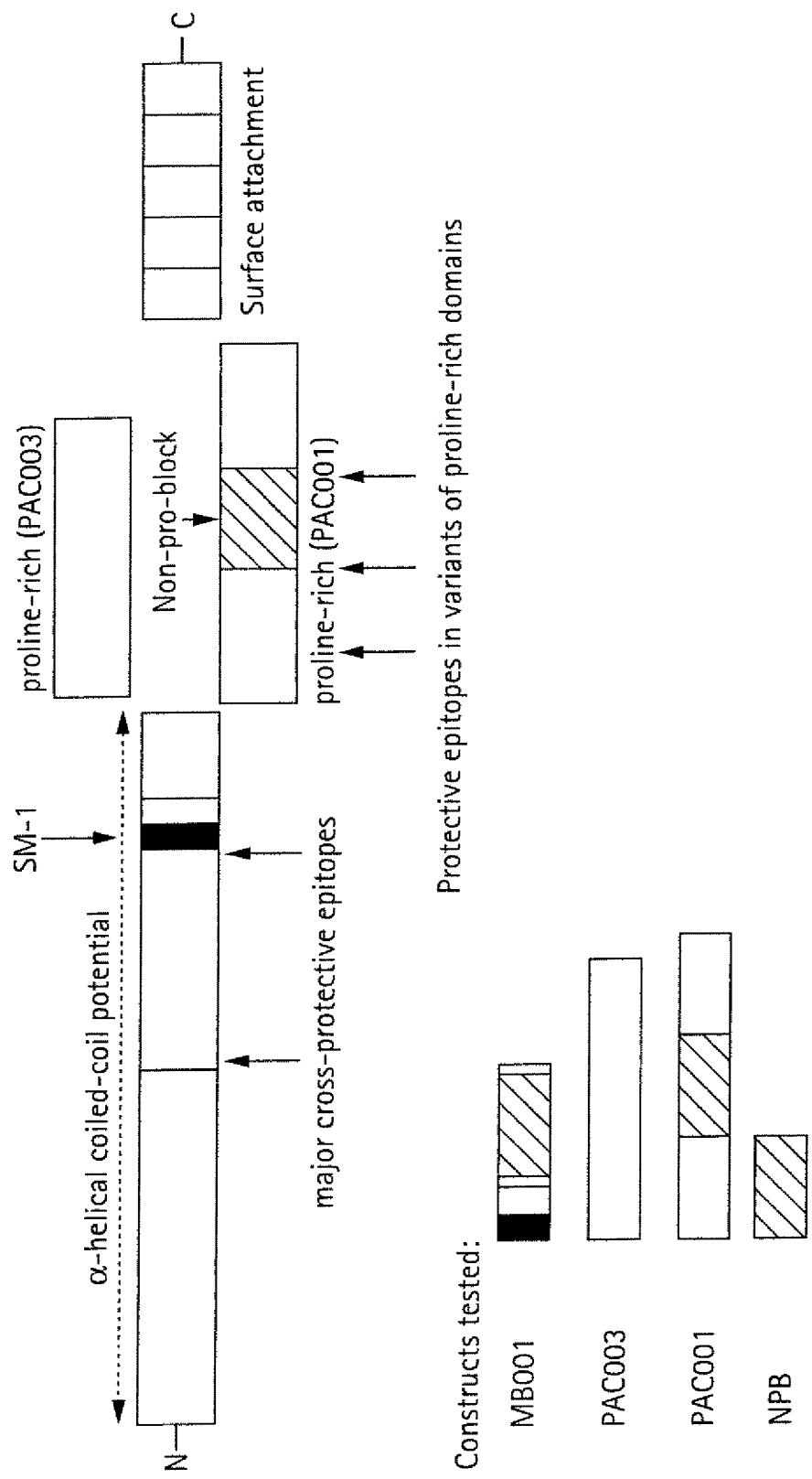
FIG. 1 depicts a map of the regions common to PspA (and in some instances PspC) proteins of all known families and clades. It also depicts recombinant Psp polypeptides MB001, PAC003, PAC001, and NPB.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. Thus, for example, the reference to a polypeptide is a reference to one or more such polypeptides, including equivalents thereof known to those skilled in the art. Other than in the operating examples, or where otherwise indicated, all numbers expressing quantities of ingredients or reaction conditions used herein should be understood as modified in all instances by the term "about." The term "about" when used in connection with percentages may mean±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of antigenic or immunogenic non-alpha helical PspA/PspC polypeptide embodiments, some methods, devices, and materials in this regard are described here.

*Streptococcus pneumoniae* are Gram-positive, lancet-shaped cocci (elongated cocci with a slightly pointed outer curvature). Usually, they are seen as pairs of cocci (diplococci), but they may also occur singly and in short chains. When cultured on blood agar, they are alpha hemolytic. Individual cells are between 0.5 micrometers and 1.25 micrometers in diameter. They do not form spores and they are non-motile. Like other streptococci, they lack catalase and ferment glucose to lactic acid. Unlike other streptococci, they do not display an M protein, they hydrolyze inulin, and their cell wall composition is characteristic both in terms of their peptidoglycan and their teichoic acid compositions.

*S. pneumoniae* is a well known human pathogen and a major etiologic agent for pneumonia, meningitis, otitis media as well as sepsis, among primarily young children and older adults. Fedson & Musher in VACCINES 2nd ED. (Plotkin & Mortimer eds., W.B. Saunders Co., Philadelphia, Pa., 1994). A capsule composed of polysaccharide completely envelops the pneumococcal cells. During invasion the capsule is an essential determinant of virulence. The capsule interferes with phagocytosis by preventing C3b opsonization of the bacterial cells. Anti-pneumococcal vaccines are based on formulations of various capsular (polysaccharide) antigens derived from the highly-prevalent strains.

*S. pneumoniae* has been divided into ninety serotypes based on its expression of serologically distinct carbohydrate capsules. Henrichsen, 33 J. CLIN. MICROBIOL. 2759-62 (1995). Antibodies to a capsular polysaccharide (PS) may provide protection against pneumococci expressing the same capsular serotype. Currently available pneumococcal vaccines contain a mixture of capsular PS of multiple serotypes. For example, one pneumococcal vaccine (called PS vaccine) contains capsular PS from twenty-three commonly found serotypes. Robbins et al., 148 J. INFECT. DIS. 1136-59 (1983). The most recently developed type of vaccine (called conjugate vaccine) contains capsular PS from seven to thirteen serotypes that are conjugated to a protein molecule. Wuorimaa & Käyhty, 56 SCAND. J. IMMUNOL. 111-29 (2002). A seven-valent conjugate vaccine was introduced in 2000 for clinical use in the United States, and has reduced the incidence of invasive pneumococcal diseases in children. Whitney, 348 N. ENGL. J. MED. 1737-46 (2003).

An alternative approach for protecting children, and also the elderly, from pneumococcal infection employs protein antigens that could elicit protective immune responses. Such proteins may serve as a vaccine by themselves, may be used in conjunction with successful polysaccharide-protein conjugates, or serve as carriers for polysaccharide components. The pneumococcal surface protein A (PspA) has been identified as a protein with potential for pneumococcal vaccines. See, e.g., U.S. Pat. No. 6,592,876; No. 6,500,613; and No. 5,997,882. Indeed, the PspA protein or portions of the protein have elicited a protective immune response following mucosal or oral administration, particularly with an adjuvant such as cholera toxin. See U.S. Pat. No. 6,042,838 and No. 6,232,116.

PspA is also an attractive target because it elicits mouse, monkey, and human antibody protective in mice; is produced by all pneumococci; interferes with complement deposition; binds lactoferrin (inhibits apolactoferrin-killing); and is serologically variable, yet cross-reactive.

Often, approaches for the use of PspA as a potential protein-based pneumococcal vaccine have focused on cross-protective epitopes found within the alpha-helical region of the PspA protein, a region predicted to have a coiled-coil protein conformation. This conformation, however, might possibly have potential to elicit antibodies that cross-react with damaged human muscle proteins from skeletal muscle and/or heart. See, e.g., Cunningham, 8 FRONT. BIOSCI. 533-43 (2003); Cunningham, 40 MOL. IMMUNOL. 1121-27 (2004); Krishner & Cunnimgham, 227 SCIENCE 413-15 (1985). Hence, this has raised concerns over using PspA as an immunogen in pneumococcal vaccines. This possibility, however, must be balanced with the observation that adult humans may have existing antibodies to PspA, that were raised naturally during the course of childhood experience with *Streptococcus pneumoniae*. These native antibodies have shown no correlation to rheumatic heart disease or auto-reactive immune syndromes.

The embodiments herein provide for immunogenic non-coiled-coil regions of PspA and PspC proteins, such as the proline-rich regions or the choline-binding region, that are less likely to elicit anti-myosin cross-reactive antibodies or to stimulate any pre-existing antibodies of this type. As used herein, PspA and PspC amino acid sequences, peptide molecules, peptides, polypeptides, proteins, and PspA or PspC portions or fragments may be used synonymously to refer to amino acid sequences encoded by the PspA or PspC gene(s) that are capable of eliciting an immune response yet lack the coiled-coil structure of myosin (although secondary or tertiary structure of the polypeptides of the present invention are certainly within the scope of the invention). Indeed, the embodiments herein provide for non-alpha-helical regions of PspA, which are also found in PspC, that are capable for eliciting protective antibodies. These smaller portions of PspA and/or PspC from within the alpha-helical regions may also lack the ability to form coiled-coils (thought to perhaps elicit myosin cross-reactive antibodies), because of their smaller size, yet retain the ability to elicit protection. These polypeptides may be harvested from pneumococcal cells or obtained using recombinant technologies well-known in the art. Hence, these PspA/PspC portions may be good candidates for protein-based pneumococcal vaccine development.

To that end, recombinant PspA/PspC polypeptides were used to immunize mice. Mice were challenged subsequently with a lethal dose of live *S. pneumoniae*. Protective responses were judged by increased survival times. These data showed that the proline-rich area of the choline-binding region of, as well as the non-pro-block of the proline rich region can elicit protection. These regions lack the coiled-coil structure implicated with a possible anti-myosin reaction.

Within the scope of the present embodiments are derivatives of the non-coiled-coil antigenic PspA and PspC polypeptides. "Derivative" is intended to include modifications of the native PspA and PspC non-alpha-coiled polypeptides that retain the either the antigenicity or immunizing activity of the native polypeptides. The term is intended to include, without limitation, portions, fragments, or complexes of the protein, peptides, polypeptides, or fusion partner proteins made by recombinant DNA or other purification techniques whose amino acid sequences are identical or substantially identical (i.e., differ in a manner that does not substantially reduce the desired level of antigenicity) to that of the protein or that of an active portion thereof, or that lack or have different substituents (e.g., lack glycosylation or differ in glycosylation), and conjugates of the protein or such fragments, oligomers, polypeptides and fusion proteins and carrier proteins. The creation and use of such polypeptides and derivatives are well-known in the art.

It is also intended that the protein coding regions for use in the present invention could also be provided by altering existing PspA or PspC genes using standard molecular biological techniques that result in variants (agonists) of the peptides described herein. Such variants include, but are not limited to deletions, additions and substitutions in the amino acid sequence of the PspA/PspC peptides, and are well-known in the art.

For example, one class of substitutions is conserved amino acid substitutions. Such substitutions are those that substitute a given amino acid in the peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent is found in Bowie et al., 247 SCIENCE 1306-10 (1990).

Variant or agonist peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 SCIENCE 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. MOL. BIOL. 899-904 (1992); de Vos et al., 255 SCIENCE 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties (2nd ed., T. E. Creighton, W. H. Freeman and Company, New York 1993). Many detailed reviews are available on this subject, such as by Wold, POSTTRANSLATIONAL COVALENT MODIFICATION OF PROTEINS, 1-12 (Johnson, ed., Academic Press, New York 1983); Seifter et al., 182 METH. ENZYMOL. 626-46 (1990); and Rattan et al., 663 ANN. N.Y. ACAD. SCI. 48-62 (1992). The secondary and tertiary structure of the peptides of the present invention may be determined by any number of techniques well-known in the art, or predicted by well-known methodologies such as Chou-Fasman secondary structure analysis as shown, for example, in FIGS. 5A-C.

Accordingly, the peptides of the present invention also encompass derivatives or analogs in which a substituted amino acid residue is not one encoded by the genetic code, in which a substituent group is included (such as pegylation) as mentioned previously.

Similarly, the additions and substitutions in the amino acid sequence as well as variations, and modifications just described may be equally applicable to the amino acid sequence of anti-PspA antibodies and/or anti-PspC antibodies that may be raised against the proteins of the present invention by methodologies well known in the art, and are thus encompassed by the present invention.

The non-alpha-helical PspA peptides and corresponding PspC peptides described herein may generate an immune response. The term "immune response" refers to a cytotoxic T-cell response and/or increased serum levels of antibodies specific to an antigen, or to the presence of neutralizing antibodies to an antigen. The immune response may indeed be sufficient to make the antigen of the invention useful as a vaccine for protecting human subjects from human pneumococcal infection. Additionally, antibodies generated by the antigen of the invention can be extracted and used to detect a bacterium in a body fluid sample. The term "protection" or "protective immunity" refers herein to the ability of the serum antibodies and/or cytotoxic T-cell response induced during immunization to protect (partially or totally) against a disease caused by an infectious agent, e.g., human *S. pneumonaie*. The use of the immunogenic polypeptides in a vaccine is expected to provide protective immunity to humans against severe pneumococcal infection by inducing antibodies against pneumococci which are known to prevent severe clinical symptoms.

In another embodiment, an immunogenic non-alpha-helical PspA/PspC peptide is conjugated to another hatpen, thus acting as an effective protein carrier or adjuvant for that hapten. Hapten refers to a disease specific antigenic determinant identified by biochemical, genetic or computational means. The haptens may be associated with a disease condition caused by *S. pneumoniae*, or by an agent such as bacteria, viruses, intracellular parasites, fungi, and transformed (cancerous or pre-cancerous) cells.

The invention includes a method of providing an immune response and protective immunity to a patient against pneumococcal-mediated diseases. The method includes administering the PspA/PspC antigen of the invention to an animal or human. The PspA/PspC antigen of the invention is preferably administered as a formulation comprising an effective amount of the antigen. A variety of physiologically acceptable carriers are known in the art, including for example, saline. Routes of administration, amounts, and frequency of administration are known to those skilled in the art for providing protective immunity to a recipient subject. Routes of administration include any method which confers protective immunity to the recipient, including, but not limited to, inhalation, intravenous, intramuscular, intraperitoneal, intradermal, and subcutaneous. Preferably the antigen of the invention is provided to a human subject by subcutaneous or intramuscular injection. A range of amounts and frequency of administration is acceptable so long as protective immunity of the recipient is achieved. For example, 5 μg to 20 μg can be administered by intramuscular injection between one four times over a three month period.

Hence, the novel immunogenic PspA/PspC polypeptides provided herein may be useful in a vaccine or in pneumococcal vaccine development. For example, the polypeptide may be incorporated into a vaccine, either alone, as a component, or as a protein carrier for a polysaccharide conjugate vaccine. See, e.g., U.S. Pat. No. 5,866,135; U.S. Pat. No. 5,773,007; and U.S. Pat. No. 6,936,252.

Antibodies raised against the PspA/PspC fragments of the present invention are also encompassed herein. For example, the monoclonal antibody designated KL67 binds to the non-pro-block portion of PspA/PspC non-alpha helical polypeptides. The ability of the anti-PpsA/PspC peptide antibodies to elicit cross-protection (protection against additional strains representing different capsular types, in which the intrinsic PspA/PspC exhibits non-identical regions to those in the vaccine) are determined by further immunization and challenge experiments using additional challenge strains to verify broad cross-protection. Sera from immunized animals such as mice and rabbits are tested for the ability to passively protect mice to determine if the protection is primarily through elicited antibody. Protection is further characterized in additional mouse models (pneumonia and carriage models), and the potential that T-cells are involved in the protection is determined.

Additionally, the smallest portions of PspA/PspC that are able to elicit protective antibodies may be identified in a mouse model of pneumococcal infection. This is done by making smaller recombinant portions, fragments, or polypeptides from the present immunogenic regions to determine the minimal effective epitopes.

Sera from immunized mice are also tested for the ability to enhance complement deposition and/or to enhance lactoferrin killing, activities that have been associated with other anti-PspA/PspC antibodies that were found to be protective. Both activities may be found to be elicited by one PspA/PspC fragment or may require more than one fragment, i.e. different fragments used in combination. These experiments may help address the assays that need to be used as correlates of protection in vaccine development.

Thus, for example, particular embodiments of the immunogenic PspA/PspC polypeptides lacking the coiled-coil structure have the amino acid sequence DLKKAVNEPE-KPAEEPENPAPAPKPAPAPQPEKPAPA-PAPKPEKSADQQAEEDYARR SEEEYNRLTQQQPP-KAEKPAPAPVPKPEQPAPAPKTGWGQENGMW [SEQ ID NO: 1]; DLKKAVNEPETPAPAPAPAPAPAPTPEA-PAPAPAPAPKPAPAPKPAPAPKPAPAPKPA PAPKPAPA-PKPAPAPAPAPKPEKPAEKPAPAPKPET-
PKTGWKQENGMW [SEQ ID NO:2]; MAKKAELEKTPEKPAEEPENPAPAPQ-
PEKSADQQAEEDYARRSEEEYNRLTQQQPPK A [SEQ ID NO: 3]; or EKSADQQAEEDYARRSEEEYNRLTQQQ [SEQ ID NO: 4].

The sequence EKSADQQAEEDYARRSEEEYNR-LTQQQ [SEQ ID NO: 4] is also referred to as the non-pro-block (NPB) having no proline amino acid residues in an otherwise proline-rich area of the non coiled region of PspA/PspC. This peptide is also identified by binding with the monoclonal antibody designated KL67, which also binds to DLKKAVNEPEKPAEEPENPAPAPKPAPA-
PQPEKPAPAPAPKPEKSADQQAEEDYARR SEEEYNR-LTQQQPPKAEKPAPAPVPKPEQPAPAPK-
TGWGQENGMW [SEQ ID NO: 1] and MAKKAELEKTPEKPAEEPENPAPAPQ-
PEKSADQQAEEDYARRSEEEYNRLTQQQPPK A [SEQ ID NO: 3]. As such, EKSADQQAEEDYARRSEEEYNR-LTQQQ [SEQ ID NO: 4] may also be considered an example portion of an immunogenic PspA/PspC peptide as disclosed herein.

Note also that the sequence, MAKKAELEKTPE-KPAEEPENPAPAPQPEKSADQQAEED-YARRSEEEYNRLTQQQPPK A [SEQ ID NO: 3], is an example of a semi-artificial variant or derivative of a native PspA/PspC sequence, having the SM-I amino acid sequence AAKKAELEKT [SEQ ID NO: 5] added to it the native sequence. See Example 1, below.

Another example variant of the NPB has the amino acid sequence MEKSADQQAEEDYARRSEEEYNRLTQQQ [SEQ ID NO: 6], which has a methionine on the amino-terminus as it may be expressed in an expression vector.

A particular embodiment provides for an immunogenic recombinant peptide comprising the amino acid sequence MEKSADQQAEEDYARRSEEEYNRLTQQQ [SEQ ID NO: 6]. A variant of this sequence, for example, with a conservative amino acid substitution in which V is substituted for A at position 5, is

```
MEKSVDQQAEEDYARRSEEEYNRLTQQQ    [SEQ ID NO: 7]
```

Figure 9:
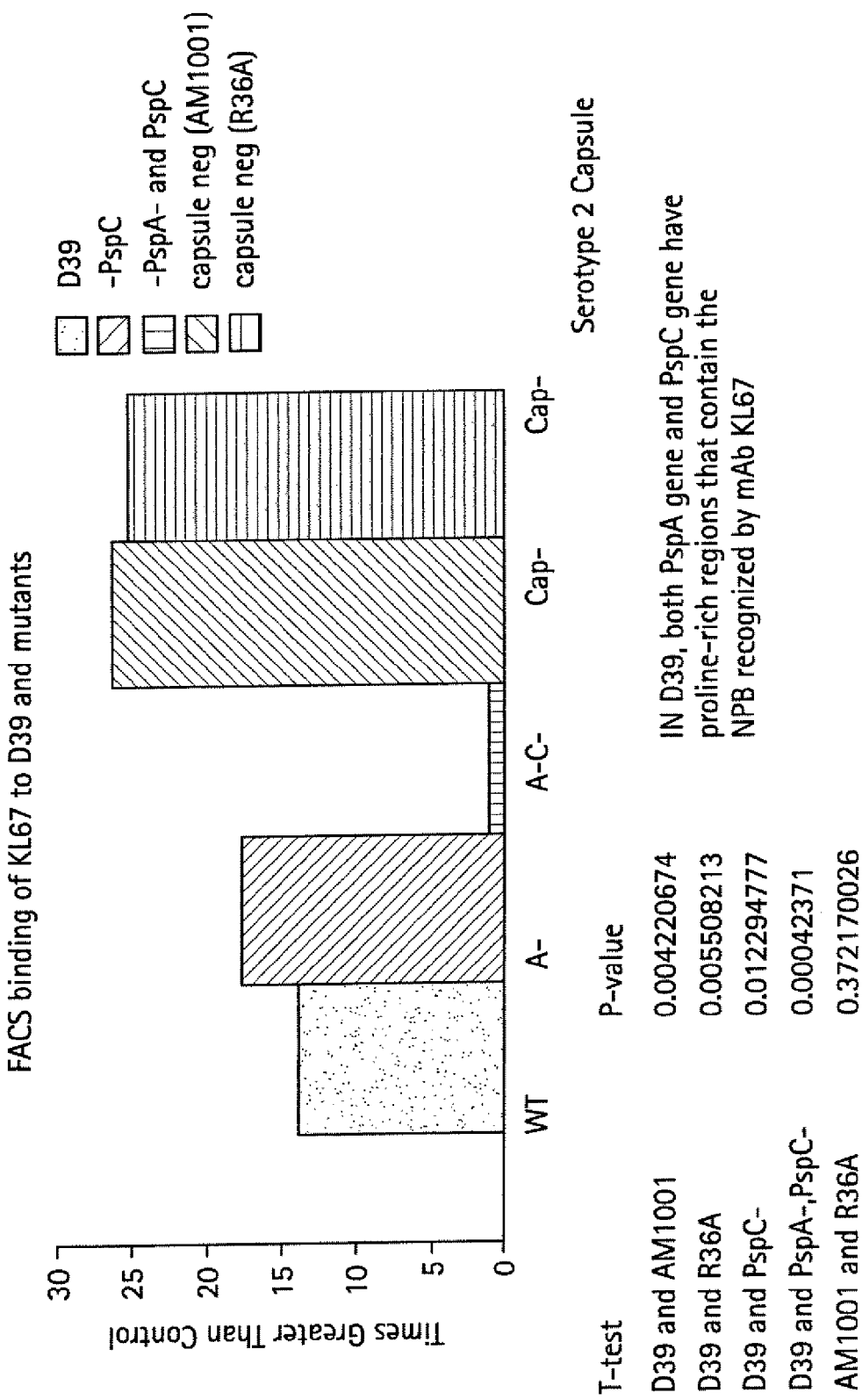
FIG. 9 presents data from fluorescent-activated cell sorting (FACS) binding of mAb KL67 to several strains of pneumococci.

Prior to the embodiments described herein, it was known that many pspA and pspC genes expressed similar structures (i.e. PAP . . . repetitive proline rich stretches—with or without the EKSADQQAEEDYARRSEEEYNRLTQQQ [SEQ ID NO: 4]. The amino acids at either end of these peptides mark the boundaries of the proline rich region. Amino-terminal to the region is DLKKAVNE . . . [SEQ ID NO: 8], carboxy-terminal to it is (K/G)TGW(K/G)QENGMW [SEQ ID NO: 9]. Peptides containing the NPB are immunogenic, suggesting that the NPB (e.g., SEQ ID NO: 4) may be an important epitope. This sequence of amino acids is also accessible to antibody binding from the surface of the bacterium, see Example 3, FIG. 9, depicting FACS data. Surface binding is likely to be important for protection, and a factor in future vaccine development.

PCR-based evidence indicates that about 77% of the pspC genes about 50% of pspA genes in isolates from Africa, Asia, and South America contain the NPB sequence (e.g., EKSADQQAEEDYARRSEEEYNRLTQQQ [SEQ ID NO: 4]) or a close homolog of this peptide. Hence these homologs represent alternative embodiments. Additionally, the NPB constitutes a common epitope present among most of the bacterial strains for which a vaccine is needed.

Nucleic acids that encode one or more of the non-alpha-helical PspA/PspC peptides, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

For example, nucleic acids (DNAs) encompassed herein include those encoding the PAC001 peptide (see Example 1, below), having the sequence:

```
                                        [SEQ ID NO: 10]
GACCTTAAGAAAGCAGTTAATGAGCCAGAAAACCAGCTGAAGAGCCTGA

GAATCCAGCTCCTGCACCAAAACCAGCGCCGGCTCCTCAACCAGAAAAC

CAGCTCCAGCTCCTGCACCAAAACCAGAGAAGTCAGCAGATCAACAAGCT

GAAGAAGACTATGCTCGTAGATCAGAAGAAGAATATAACCGCTTGACTCA

ACAGCAACCGCCAAAAGCAGAAAAACCAGCTCCAGCTCCTGTACCAAAAC

CAGAGCAACCAGCTCCCGCACCAAAAACGGGCTGGGGACAAGAAAACGGT

ATGTGG
```

An example DNA encoding the PAC003 peptide has the sequence:

```
                                        [SEQ ID NO: 11]
GACCTTAAGAAAGCAGTTAATGAGCCAGAAACTCCAGCTCCGGCTCCAGC

CCCAGCTCCAGCTCCAGCTCCAACTCCAGAAGCCCCAGCTCCAGCTCCAG

CTCCGGCTCCTAAACCAGCTCCGGCTCCTAAACCAGCTCCGGCTCCTAAA

CCAGCTCCGGCTCCTAAACCAGCTCCGGCTCCTAAACCAGCTCCGGCTCC

TAAACCAGCTCCAGCTCCAGCTCCGGCTCCTAAACCAGAAAAGCCAGCAG

AAAAACCAGCTCCAGCTCCTAAACCAGAAACTCCAAAAACAGGCTGGAAA

CAAGAAAACGGTATGTGG
```

An example DNA encoding the MB001 peptide has the sequence:

```
                                        [SEQ ID NO: 12]
ATGGCTAAAAAAGCTGAATTAGAAAAAACTCCAGAAAAACCAGCTGAAGA

GCCTGAGAATCCAGCTCCAGCACCACAACCAGAGAAGTCAGCAGATCAAC

AAGCTGAAGAAGACTATGCTCGTAGATCAGAAGAAGAATATAATCGCTTG

ACCCAACAGCAACCGCCAAAAGCA
```

An example DNA encoding a NPB (from MB001) has the sequence:

```
                                        [SEQ ID NO: 13]
GAGAAGTCAGCAGATCAACAAGCTGAAGAAGACTATGCTCGTAGATCAGA

AGAAGAATATAATCGCTTGACCCAACAGCAACCG
```

Another example DNA encoding a NPB (in PAC001) has the sequence:

```
                                        [SEQ ID NO: 14]
   GAGAAGTCAGCAGATCAACAAGCTGAAGAAGACTATGCTCGTAGAT

CAGAAGAAGAATATAACCGCTTGACTCAACAGCAACCG
```

The invention will now be described further by non-limiting examples.

EXAMPLES

Example 1

Recombinant PspA Polypeptides

Recombinant plasmids producing some of the relevant PspA polypeptides were generated and used to provide purified rPspA proteins. The proteins made are indicated in FIG. 1, and detailed amino acid sequences are given in FIGS. 2A-E and FIGS. 3A-D. Briefly, the expression vectors include a thioredoxin gene (trx) from mouse. The gene fragment encoding the peptide of interest is cloned in such a way that it makes a protein fusion with the thioredoxin. In FIGS. 2A-E, the non-underlined amino acids came from the vector. The underlined amino acids came from the cloned portion. The PET32A and PET32B proteins are referred to as "fusion partner."

Construction of the Clone pPAC001 and Purification of PspA/AC94$_{AAPro-rich}$.

The protein is called PAC001 (or PspA/AC94Pro). This recombinant protein contains the proline-rich region of the pspA gene from strain AC94. This is a proline-rich region that has a NPB in the center of two proline-rich stretches of amino acids. The NPB has the amino acid sequence DQQAEED-YARRSEEEYNRLTQQQ [SEQ ID NO: 15]. Robinson et al., 2001.

Construction of vector. An internal gene fragment of the pspA.AC94 gene (see Robinson et al., *Clones of Streptococcus pneumoniae isolated from nasophayngeal carriage and invasive disease in young children in Tennessee*, 183 J. INFECT. DIS. (2001)) encoding PspA/AC94pro was amplified by polymerase chain reaction from the *Streptococcus pneumoniae* strain AC94 using the oligonucleotides 5'GGGAG CCATGGCTGACCTTAAGAAAGCAGTTAATGAGCCA3' [SEQ ID NO: 16] (pspA27-NcoI) and 5'CC GTCGACACCACATACCGTTTTCTTGTTTCCAGCC3' [SEQ ID NO: 17] (pspA22-SalI) (restriction endonuclease (RE) recognition sites underlined). Reactions were carried out for 30 cycles in a total volume of 50 ml in a cocktail containing 3.0 mM MgCl2, 125 mM dNTPs, 50 picomole of each primer, and 2.5 units of Taq DNA Polymerase. The cycle was 94° C., 1 min.; 55° C., 1 min.; 72° C., 5 min. This amplified gene fragment was digested with NcoI and SalI, and the ~300 bp pspA gene fragment was then incorporated between NcoI and SalI sites of a vector (pET32a, Novagen, Inc.) with a strong T7 promoter and translation signals. DNA sequence confirmed that the recombinant plasmid pPAC001 contained the expected 315 kbp pspA gene fragment inserted after the trx gene and the His-tag site in vector pET32a.

The plasmid pPAC001 was transformed into the *E. coli* strain BL21 STAR (DE3) for protein production. This strain contains a chromosomal copy of the T7 promoter under control of the inducible UV5 promoter. Upon induction with IPTG, a recombinant protein that contains 283 amino acids, 105 of which derive from the proline-rich region of PspA protein, is expressed. The rPAC001 is a protein fusion between thioredoxin (from vector) and the proline-rich region. The sequence of the complete recombinant protein is given below (italics proline insert only). The six histidine residues present in the middle of the recombinant protein are used to simplify its purification by nickel chromatography. It can also be cleaved with enterokinase to allow its release from the trx fusion partner. The protein was made in this fashion to ensure immunogenicity because of the small size of the PspA-specific portion. The rPET32a protein (mostly thioredoxin) is used as a negative control immunogen in immunization protocols.

The protein sequence of the insert is:

[SEQ ID NO: 18]
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGHMHHHHHHSSGLVPRGSGMKETAAAKFERQHMDSPD

LGTDDDDK*AMADLKKAVNEPEKPAEEPENPAPAPKPAPAPQPEKPAPAPA*

*PKPEKSADQQAEEDYARRSEEEYNRLTQQQPPKAEKPAPAPVPKPEQPAP*

*APKTGWGQENGMW*CRQACGRTRAPPPPPLRSGC

The thioredoxin gene and the His tag, plus some sequences the N-terminal end and the C-terminal end are from the pET32a vector. The total amino acid composition is included herein, the 105 amino acids in italics, above, are the native PspA amino acids. Note that about one-quarter of these amino acids are proline.

The DNA sequence of the PCR product before cutting with NcoI and SalI is:

[SEQ ID NO: 19]
xxxCCATGGCTGACCTTAAGAAAGCAGTTAATGAGCCAGAAAAACCAGCT

GAAGAGCCTGAGAATCCAGCTCCTGCACCAAAACCAGCGCCGGCTCCTCA

ACCAGAAAAACCAGCTCCAGCTCCTGCACCAAAACCAGAGAAGTCAGCAG

ATCAACAAGCTGAAGAAGACTATGCTCGTAGATCAGAAGAAGAATATAAC

CGCTTGACTCAACAGCAACCGCCAAAAGCAGAAAAACCAGCTCCAGCTCC

TGTACCAAAACCAGAGCAACCAGCTCCCGCACCAAAAACGGGCTGGGGAC

AAGAAAACGGTATGTGGGTCGACxxx

This includes the NcoI sites and SalI sites that were on the primers. (RE sites underlined in above sequence).

An example nucleic acid (DNA) encoding the PAC001 polypeptide has the sequence:

[SEQ ID NO: 10]
GACCTTAAGAAAGCAGTTAATGAGCCAGAAAAACCAGCTGAAGAGCCTGA

GAATCCAGCTCCTGCACCAAAACCAGCGCCGGCTCCTCAACCAGAAAAAC

CAGCTCCAGCTCCTGCACCAAAACCAGAGAAGTCAGCAGATCAACAAGCT

GAAGAAGACTATGCTCGTAGATCAGAAGAAGAATATAACCGCTTGACTCA

ACAGCAACCGCCAAAAGCAGAAAAACCAGCTCCAGCTCCTGTACCAAAAC

CAGAGCAACCAGCTCCCGCACCAAAAACGGGCTGGGGACAAGAAAACGGT

ATGTGG

An example nucleic acid encoding the NPB within the PAC001 polypeptide has the sequence:

[SEQ ID NO: 14]
GAGAAGTCAGCAGATCAACAAGCTGAAGAAGACTATGCTCGTAGATCAGA

AGAAGAATATAACCGCTTGACTCAACAGCAACCG

Calculated Molecular Weight = 30531.77
Estimated pI = 5.56
Amino Acid Composition:

|   | No. | Percent |
|---|---|---|
| Non-polar: | | |
| A | 36 | 12.72 |
| V | 8 | 2.83 |
| L | 18 | 6.36 |
| I | 9 | 3.18 |
| P | 37 | 13.07 |
| M | 7 | 2.47 |

-continued

Calculated Molecular Weight = 30531.77
Estimated pI = 5.56
Amino Acid Composition:

|   | No. | Percent |
|---|---|---|
| F | 5 | 1.77 |
| W | 4 | 1.41 |
| Polar: | | |
| G | 21 | 7.42 |
| S | 12 | 4.24 |
| T | 11 | 3.89 |
| C | 5 | 1.77 |
| Y | 4 | 1.41 |
| N | 8 | 2.83 |
| Q | 13 | 4.59 |
| Acidic: | | |
| D | 20 | 7.07 |
| E | 22 | 7.77 |
| Basic: | | |
| K | 24 | 8.48 |
| R | 10 | 3.53 |
| H | 9 | 3.18 |

An ELISA method is used to determine antibody titers to PspA proline-rich portion. Initial tests of this antigen in ELISA, and antibody response directed at the fusion partner protein (pET32a), are measured. An inhibition ELISA in which most of the pET32a-specific response is inhibited is used in order to get data of PspA-specific response. Based upon total protein concentrations determined by the Biorad protein assay, Nunc MaxiSorp plates (Nalge Nunc Int'l, Denmark) are coated with 3 μg per ml of the recombinant protein in phosphate buffered saline overnight. Control wells are coated with a similar amount of pET32a alone. A 1:1000 dilution of a mouse is used in ELISA. Non-specific reactivity is inhibited by adding 3-10 ug/mL of pET32a protein in with the sera diluent. This is constant across the sera dilution.

Additional references relating to PspA clades and families include Hollingshead et al., 68 INFECT. IMMUN. 5889-900 (2000); Briles et al., 182 J. INFECT. DIS. 1694-1791 (2000); and Briles et al., 18 VACCINE 1707-11 (2000). Further information relating to the pspC gene is available, for example, see Brooks-Walter et al., 67 INFECT. IMMUN. 6533-6542 (1999).

Construction of the Clone pPAC003 and Purification of PspA/BG9739$_{AAPro-rich}$ The protein is called PAC003 (or PspA/BG9739$_{Pro}$). This recombinant protein contains the proline-rich region of the pspA gene from strain BG9739. This is a proline-rich regions that does not have a NPB in the center of two proline-rich stretches of amino acids. The NPB was that of SEQ ID NO: 15. The NPB is an immunogenic section of PspA, hence the inventors differentiate whether protective antibodies react with proline-rich epitopes or perhaps others in this region using this construct.

In constructing a vector, an internal gene fragment of the pspA.BG9739 gene encoding PspA/BG9739Pro, was amplified by polymerase chain reaction from the S. pneumoniae strain BG9739 using the oligonucleotides of SEQ ID NO: 16 and SEQ ID NO: 17. Reactions were carried out as with the construction of pPAC001. DNA sequence confirmed that the recombinant plasmid pPAC003 contained the expected 334 kbp pspA gene fragment inserted after the trx gene and the His-tag site in vector pET32a.

The plasmid pPAC003 was transformed into the E. coli strain BL21 AI (DE3) for protein production. This strain contains a chromosomal copy of the T7 promoter under control of the inducible araBAD promoter. Upon induction with arabinose and IPTG, a recombinant protein that contains 288 amino acids, 110 of which derive from the proline-rich region of PspA_BG9739 protein, is expressed. The rPAC003 is a protein fusion between thioredoxin (from vector) and the proline-rich region. The sequence of the complete recombinant protein is given below (italics proline insert only). The six histidine residues present in the middle of the recombinant protein are used to simplify its purification by nickel chromatography. It can also be cleaved with enterokinase to allow its release from the trx fusion partner. The protein was made in this fashion to ensure immunogenicity because of the small size of the PspA-specific portion. The rPET32a protein (mostly thioredoxin) is used as a negative control immunogen in immunization protocols.

The protein sequence of the insert is:

[SEQ ID NO: 20]
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGHMHHHHHHSSGLVPRGSGMKETAAAKFERQHMDSPD

LGTDDDDK*AMADLKKAVNEPETPAPAPAPAPAPAPTPEAPAPAPAPAPKP*

*APAPKPAPAPKPAPAPKPAPAPKPAPAPKPAPAPAPAPKPEKPAEKPAPA*

*PKPETPKTGWKQENGMW*CRQACGRTRAPPPPPLRSG

The thioredoxin gene and the His tag, plus a bit more at the N-terminal end and a bit at the C-terminal end are coming from the pET32a vector. The total amino acid composition follows below. Of the amino acid sequence above, 109 (in italics, above) are the native PspA amino acids. About one-third of that is proline. The DNA sequence of the PCR product before cutting with NcoI and SalI is:

[SEQ ID NO: 21]
xxxCATGGCTGACCTTAAGAAAGCAGTTAATGAGCCAGAAACTCCAGCTC

CGGCTCCAGCCCCAGCTCCAGCTCCAGCTCCAACTCCAGAAGCCCCAGCT

CCAGCTCCAGCTCCGGCTCCTAAACCAGCTCCGGCTCCTAAACCAGCTCC

GGCTCCTAAACCAGCTCCGGCTCCTAAACCAGCTCCGGCTCCTAAACCAG

CTCCGGCTCCTAAACCAGCTCCAGCTCCAGCTCCGGCTCCTAAACCAGAA

AAGCCAGCAGAAAACCAGCTCCAGCTCCTAAACCAGAAACTCCAAAAAC

AGGCTGGAAACAAGAAAACGGTATGTGGTGTCGACxxx

This includes the NcoI sites and SalI sites that were on the primers (RE sites underlined in above sequence).

A relevant nucleic acid (DNA) encoding the PAC003 polypeptide has the sequence:
[SEQ ID NO: 11]
GACCTTAAGAAAGCAGTTAATGAGCCAGAAACTCCAGCTCCGGCTCCAGC

CCCAGCTCCAGCTCCAGCTCCAACTCCAGAAGCCCCAGCTCCAGCTCCAG

CTCCGGCTCCTAAACCAGCTCCGGCTCCTAAACCAGCTCCGGCTCCTAAA

CCAGCTCCGGCTCCTAAACCAGCTCCGGCTCCTAAACCAGCTCCGGCTCC

TAAACCAGCTCCAGCTCCAGCTCCGGCTCCTAAACCAGAAAAGCCAGCAG

AAAAACCAGCTCCAGCTCCTAAACCAGAAACTCCAAAAACAGGCTGGAAA

CAAGAAAACGGTATGTGG

Calculated Molecular Weight = 29795.33
Estimated pI = 8.48
Amino Acid Composition:

|   | No. | Percent |
|---|---|---|
| Non-polar: | | |
| A | 48 | 16.78 |
| V | 7 | 2.45 |
| L | 17 | 5.94 |
| I | 9 | 3.15 |
| P | 53 | 18.53 |
| M | 7 | 2.45 |
| F | 5 | 1.75 |
| W | 4 | 1.40 |
| Polar: | | |
| G | 20 | 6.99 |
| S | 10 | 3.50 |
| T | 13 | 4.55 |
| C | 4 | 1.40 |
| Y | 2 | 0.70 |
| N | 6 | 2.10 |
| Q | 6 | 2.10 |
| Acidic: | | |
| D | 18 | 6.29 |
| E | 14 | 4.90 |
| Basic: | | |
| K | 27 | 9.44 |
| R | 7 | 2.45 |
| H | 9 | 3.15 |

This construct may be used to test whether this portion of PspA can elicit protective antibodies in animal model systems and in humans. Additionally, this is useful to test how broad the protection is (e.g., can it protect against strains with different PspA/PspC proteins). It may differentiate between proline-rich epitopes and others that may fall in this region of the PspA protein.

Construction of the Clone pMB001 and Purification of PspA$_{SM-1\_Pro-rich}$.

The protein is called MB001 (or PspASM-1_non-pro-block). This recombinant protein contains both the non-pro-block (Brooks-Walter et al., 1999) present in some of the proline-rich regions of the pspA gene along with the peptide SM-1 (Shaper et al., 72 Infect. Immun. 5031-40 (2004)), and some small remnants from the proline-rich segment. The NPB has the amino acid sequence of SEQ ID NO: 15 and the sequence called SM-1 is

```
AAKKAELEKT.          [SEQ ID NO: 7]
```

These two regions were of interest because of the following observations: (1) Non-pro block: in immunizations with various rPspC proteins, many of which contained this block, the inventors were able to immunize and protect against challenge strains which lacked PspC but had a PspA with a very similar non-pro-block. Using UAB055 and UAB103 (two proteins that differ only by the non-pro-block) in ELISA, it was found that immunization with rPspC elicited antibodies that reacted with the non-pro-block in UAB103. Some screens of the cross-reactivity among various BC100-type antiseras suggested that the non-pro block was more immunogenic than the specific proline-rich segments around it. The block was present in 15/24 PspA genes sequenced and in 10/12 PspC genes sequenced; (2) SM-1 peptide: it has been found that apo-lactoferrin can kill pneumococci, but this killing could be inhibited by the SM-1 peptide (but not by other peptides). This peptide may (or may not) represent the region where PspA binds to lactoferrin. This small region is the best conserved segment of the alignment between four clades of PspA:

```
                                     [SEQ ID NO: 22]
Clade 1 I . . . AKKAELEKA . . . EAD
                                     [SEQ ID NO: 23]
Clade 2 A . . . AKKAELEKT . . . EAD
                                     [SEQ ID NO: 24]
Clade 3 A . . . TKKAELEKT . . . QKE
                                     [SEQ ID NO: 25]
Clade 4 A . . . TKKAELEKT . . . QKE
```

(3) Region related to proline-rich segments in pMB001: this construct also has the following small segment PEKPAEEP-ENPAPAPQPEKS [SEQ ID NO: 26], which came from a Brazilian strain. Each proline-rich segment may differ between strains, but PAPAP [SEQ ID NO: 27] and PEKPA [SEQ ID NO: 28] are often seen in reiterative patterns. Another cloned protein, PAC003, addresses the antigenicity of this region.

In constructing a vector, an internal gene fragment was cut using EcoRI from a previous clone (see below). pET32b was cut with EcoRI and phosphatased. The two were ligated together and transformants were screened for the proper orientation. The screen was done using primer 5' GGTACCTGCTTTTGGCGGTTGCTG3' [SEQ ID NO: 29] CL1pro1. Together with T7prom primer, this gives about a 783 bp PCR fragment in the proper orientation. In this orientation it makes the fusion protein presented below.

Sequences relevant to pMB001, PspA specific portion

```
Xho 1
                                          [SEQ ID NO: 30]
5' CTC GAG ATG GCT AAA AAA GCT GAA TTA GAA AAA ACT

CCA GAA AAA CCA GCT GAA GAG CCT GAG AAT CCA GCT

TCA GCA CCA CAA CCA CAA CAA GCT GAA GAA GAC TAT

GCT CGT AGA TCA GAA GAA GAA TAT AAT CGC TTG ACC

CAA GCA GGA AAA ACC AGC 3'
```

Because this fragment was cut by EcoRI from pGem-T, this piece was inserted into the EcoR1-cut pET32b to make pMB001. Orientation was checked with primers CL1pro1—together with T7prom (yielding about a 783 bp PCR fragment). In this orientation—it makes the fusion protein below:

```
                                                            [SEQ ID NO: 31]
     EcoR1           Xho1
5' GAATTCACTAGTGATT CTC GAG ATG GCT AAA AAA GCT GAA TTA GAA
                     L   E   M   A   K   K

AAA ACT CCA GAA AAA CCA GCT GAA GAG CCT GAG AAT CCA GCT CCA GCA CCA CAA CCA
```

-continued

```
GAG AAG TCA GCA GAT CAA CAA GCT GAA GAA GAC TAT GCT CGT AGA TCA GAA GAA GAA

TAT AAT CGC TTG ACC CAA CAG CAA CCG CCA AAA GCA GGT ACC AATCGAATTC
  EcoR1                                              Kpn 1
```

Protein produced in pMB001:

[SEQ ID NO: 32]
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGH<u>MHHHHHHSSGLVPRGSGMKETAAAKFERQHMDSPD</u>

<u>LGTDDDDKAMAISDPNS</u>LVILEMAKKAELEKTPEKPAEEPENPAPAPQPE

KSADQQAEEDYARRSEEEYNRLTQQQPPKAGTNRI*RAPSTSLRPHSSTTT*

*TTTEIRLLTKPERKLSWLLPPLSNN*

Of the amino acids presented above, the italics signify the trx protein; underline designates the His-tag_thrombin_S-Tag_enterokinase region; plain text shows the portion carried along from pGEM-T; and bold signifies the PspA-related portion, containing the SM1 peptide and part of a proline region.

In this instance, the DNA sequence confirmed that the recombinant plasmid pMB001 contains the 162 bp from pspA genes (two discontinuous fragments) which are inserted after the trx gene and the His-tag site in vector pET32b. These lead to 54 AA of PspA in the final recombinant protein.

pMB001 was transformed into the *E. coli* strain BL21 STAR (DE3) for protein production. This strain contains a chromosomal copy of the T7 promoter under control of the inducible UV5 promoter. Upon induction with IPTG, a recombinant protein that contains 275 amino acids, 54 of which derive from the PspA protein, is expressed. The rPAC001 is a protein fusion between thioredoxin (from vector) and the proline-rich region. The sequence of the complete recombinant protein is given below (italics proline insert only). The six histidine residues present in the middle of the recombinant protein are used to simplify its purification by nickel chromatography. It can also be cleaved with enterokinase to allow its release from the trx fusion partner. The protein was made in this fashion to ensure immunogenicity because of the small size of the PspA-specific portion. The rPET32a protein (mostly thioredoxin) is used as a negative control immunogen in immunization protocols.

An example nucleic acid (DNA) encoding the MB001 polypeptide has the sequence:

[SEQ ID NO: 12]
ATGGCTAAAAAAGCTGAATTAGAAAAAACTCCAGAAAAACCAGCTGAAGA

GCCTGAGAATCCAGCTCCAGCACCACAACCAGAGAAGTCAGCAGATCAAC

AAGCTGAAGAAGACTATGCTCGTAGATCAGAAGAAGAATATAATCGCTTG

ACCCAACAGCAACCGCCAAAAGCA

Additionally, an example nucleic acid (DNA) encoding the NPB peptide has the sequence:

[SEQ ID NO: 13]
GAGAAGTCAGCAGATCAACAAGCTGAAGAAGACTATGCTCGTAGATCAGA

AGAAGAATATAATCGCTTGACCCAACAGCAACCG

Calculated Molecular Weight = 30141.38
Estimated pI = 5.40
Amino Acid Composition:

| | No. | Percent |
|---|---|---|
| Non-polar: | | |
| A | 27 | 9.82 |
| V | 7 | 2.55 |
| L | 26 | 9.45 |
| I | 13 | 4.73 |
| P | 22 | 8.00 |
| M | 7 | 2.55 |
| F | 5 | 1.82 |
| W | 3 | 1.09 |
| Polar: | | |
| G | 17 | 6.18 |
| S | 19 | 6.91 |
| T | 19 | 6.91 |
| C | 2 | 0.73 |
| Y | 4 | 1.45 |
| N | 10 | 3.64 |
| Q | 10 | 3.64 |
| Acidic: | | |
| D | 20 | 7.27 |
| E | 22 | 8.00 |
| Basic: | | |
| K | 21 | 7.64 |
| R | 11 | 4.00 |
| H | 10 | 3.64 |

This construct is used to test whether adding a portion of PspA (SM-1, in particular) may elicit superior protective antibodies in animal model systems and in humans as compared to immunogens that contain the proline-rich subsections alone (such as PAC001 or PAC003). The breadth of protection (e.g., can it protect against strains with different PspAs) may also be determined.

Construction of the Clone pCD1_NPB and Purification of GST_NPB Peptide

The expressed from this construct is called GST_NPB (or, alternatively, NPB Protein). This recombinant protein contains the NPB that is embedded in the proline-rich region of some PspA and some PspC genes. This particular construct was cloned from pPAC001 (strain AC94). An amino acid sequence referred to as the NPB is, for example, MEK-SADQQAEEDYARRSEEEYNRLTQQQ[SEQ ID NO: 6]. It appears that this NPB is a highly immunogenic section in this polypeptide, and may raise antibodies that are protective and that bind the surface of encapsulated cells.

The vector was constructed as follows: An internal gene fragment of the PspA/AC94pro gene encoding PspA/AC94pro, was amplified by polymerase chain reaction from the pPAC001 plasmid using the oligonucleotides 5'-GACGACGACAAGATGGAG AAGTCAGCAGATCAA-3' [SEQ ID NO: 33] (non-pro-L5) and 5'-GAGGAGAAGCCCGGTTTACCGTTGCTGTTGAGTCA-AGCG3' [SEQ ID NO: 34] (non-pro-R3-corrected). The corrected sequence added the TTA to provide a stop codon. PCR reactions were carried out for 30 cycles in a total volume of 50 ml in a cocktail containing 3.0 mM MgCl$_2$, 125 mM dNTPs, 0.4 umol final concentration of each primer, and 0.4 units of KOD DNA Polymerase. The amplicon from this reaction was treated with T4 DNA polymerase as per pET41 man'facturer's protocol. The cycle was 94° C., 1 min.; 55° C., 1 min; 72° C., 5 minutes. This amplified gene fragment was incorporated by ligation independent cloning at the EK/LIC site of a vector (pET41 EK/LIC, Novagen, Inc.) with a strong T7 promoter and translation signals. DNA sequence confirmed that the recombinant plasmid pCD_NPB containing the expected ~117 bp pspA gene fragment inserted after the GST gene and the His-tag site in vector pET41 EK/LIC.

The plasmid pCD_NPB was transformed into the *E. coli* strain BL21 STAR (DE3) for protein production. This strain contains a chromosomal copy of the T7 promoter under control of the inducible UV5 promoter. Upon induction with IPTG, a recombinant protein that contains 307 amino acids, 28 of which derive from the proline-rich region of PspA protein, is expressed. The rCD_NPB is a protein fusion between glutathione-S-transferase (GST-Tag) (from vector) and the non-pro-block of the proline-rich region. The sequence of the complete recombinant protein is given below (underlined). The six histidine residues present in the middle of the recombinant protein are used to simplify its purification by nickel chromatography. It can also be cleaved with thrombin or enterokinase to allow its release from the GST fusion partner. The protein was made in this fashion to ensure immunogenicity because of the small size of the PspA-specific portion. The rPET41 protein (mostly GST) is used as a negative control immunogen in immunization protocols.

The protein sequence of the insert is:

[SEQ ID NO: 35]
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDGSTSGSGHHHHHHSAGLVPRGSTAIGMKET

AAAKFEROHMDSPDLGTGGGSGDDDDKMEKSADQQAEEDYARRSEEEYNR

LTQQQP

The GST gene, the His tag, the thrombin site, the S-Tag, plus a bit more at the N-terminal end are coming from the pET41 Ek/LIC vector. The total amino acid composition is presented. Twenty-eight of the amino acids (plain text, not underlined) are the native PspA amino acids from the non-pro-block.

The DNA sequence of the PCR product with LIC ends before using T4 DNA polymerase to exonucleolytically digest the ends was:

[SEQ ID NO: 36]
GACGACGACAAGATGGAGAAGTCAGCAGATCAACAAGCTGAAGAAGACTA

TGCTCGTAGATCAGAAGAAGAATATAATCGCTTGACCCAACAGCAACCGT

AAACCGGGCTTCTCCTC

This includes the LIC sites that were on the primers (RE sites underlined in above sequence).

Calculated Molecular Weight = 34983.93
Estimated pI = 5.58
Amino Acid Composition:

| | No. | Percent |
|---|---|---|
| Non-polar: | | |
| A | 18 | 5.88 |
| V | 10 | 3.27 |
| L | 30 | 9.80 |
| I | 14 | 4.58 |
| P | 16 | 5.23 |
| M | 12 | 3.92 |
| F | 10 | 3.27 |
| W | 4 | 1.31 |
| Polar: | | |
| G | 25 | 8.17 |
| S | 18 | 5.88 |
| T | 11 | 3.59 |
| C | 4 | 1.31 |
| Y | 16 | 5.23 |
| N | 5 | 1.63 |
| Q | 11 | 3.59 |
| Acidic: | | |
| D | 26 | 8.50 |
| E | 24 | 7.84 |
| Basic: | | |
| K | 25 | 8.17 |
| R | 14 | 4.58 |
| H | 13 | 4.25 |

The similarity of the non-pro-block in multiple pspA and pspC genes is indicated in FIGS. 12A-B. These polypeptides, having homologous sequences, also fall within the scope of the immunogenic non-alpha-coiled PspA/PspC polypeptide embodiments described herein. The variations in these amino acid sequences may also be considered derivatives, variants, or portions of the immunogenic polypeptides described herein.

Construction of the Clone pCD42_NPB and Purification of GST_NPB Peptide

The protein expressed from this clone was designated GST_NPB (or NPB Protein). This recombinant protein contains the NPB that is embedded in the proline-rich region of some pspA and some pspC genes. This particular one was cloned from pPAC001 (strain AC94). The amino acid sequence of the NPB in this construct is MEK-SADQQAEEDYARRSEEEYNRLTQQQ [SEQ ID NO: 6]. The NPB is immunogenic, antibodies to it are protective and also bind from the surface of encapsulated cells.

Construction of vector. An internal gene fragment of the PspA/AC94Pro gene1 encoding PspA/AC94Pro, was amplified by polymerase chain reaction from the pPAC001 plasmid using the oligonucleotides 5' GACGACGACAAGATG-GAGAAGTCAGCAGAT CAA3' [SEQ ID NO: 37] (non-pro-L5) and 5'GAGGAGAAGCCCGGTTTACCGTTGCTG TTGAGTCAAGCG3' [SEQ ID NO: 38] (non-pro-R3-corrected). The correction added TTA to provide a stop codon. PCR reactions were carried out for 30 cycles in a total volume of 50 ml in a cocktail containing 3.0 mM MgCl2, 125 mM dNTPs, 0.4 umol final concentration of each primer, and 0.4 units of KOD DNA Polymerase. The amplicon from this reaction was treated with T4 DNA polymerase as per pET41 manufacturer's protocol. The cycle was 94° C., 1 min.; 55° C., 1 min; 72° C., 5 min. This amplified gene fragment was incorporated by ligation independent cloning at the EK/LIC site of a vector (pET41 EK/LIC, Novagen, Inc.) with a strong T7 promoter and translation signals. DNA sequencing confirmed that the recombinant plasmid pCD_NPB containing the expected ~117 bp pspA gene fragment inserted after the GST gene and the His-tag site in vector pET41 EK/LIC.

The plasmid pCD42_NPB was transformed into the *E. coli* strain BL21 STAR (DE3) for protein production. This strain contains a chromosomal copy of the T7 promoter under control of the inducible UV5 promoter. Upon induction with IPTG, a recombinant protein that contains 307 amino acids, 28 of which derive from the proline-rich region of PspA protein, is expressed. The rCD_NPB is a protein fusion between glutathione-S-transferase (GST-Tag) (from vector) and the non-pro-block of the proline-rich region. The sequence of the complete recombinant protein is given below (italics insert only). The six histidine residues present in the middle of the recombinant protein are used to simplify its purification by nickel chromatography. It can also be cleaved with thrombin or enterokinase to allow its release from the GST fusion partner. The protein was made in this fashion to ensure immunogenicity because of the small size of the PspA-specific portion. The rPET41 protein (mostly GST) is used as a negative control immunogen in immunization protocols.

The protein sequence of the insert is:

[SEQ ID NO: 39]
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDGSTSGSGHHHHHHSAGLVPRGSTAIGMKET

AAAKFERQHMDSPDLGTGGGSGDDDDKMEKSADQQAEEDYARRSEEEYNR

LTQQQP

The GST gene, the His tag, the thrombin site, the S-Tag, plus a bit more at the N-terminal end come from the pET41 Ek/LIC vector. Analysis of the total amino acid composition is below. Twenty-eight above amino acids, shown in bold, are native PspA amino acids from the NPB. The DNA sequence of the PCR product with LIC ends (in italics) before using T4 DNA polymerase to exonucleolytically digest the ends was:

[SEQ ID NO: 40]
GACGACGACAAGA*TGGAGAAGTCAGCAGATCAACAAGCTGAAGAAGACTA*

*TGCTCGTAGATCAGAAGAAGAATATAATCGCTTGACCCAACAGCAACCGT*

*AAACCGGGCTTCTCCTC*

| Calculated Molecular Weight = 34983.93 |
| Estimated pI = 5.58 |
| Amino Acid Composition: |

|  | No. | Percent |
|---|---|---|
| Non-polar: | | |
| A | 18 | 5.88 |
| V | 10 | 3.27 |
| L | 30 | 9.80 |
| I | 14 | 4.58 |
| P | 16 | 5.23 |
| M | 12 | 3.92 |
| F | 10 | 3.27 |
| W | 4 | 1.31 |

-continued

| Calculated Molecular Weight = 34983.93 |
| Estimated pI = 5.58 |
| Amino Acid Composition: |

|  | No. | Percent |
|---|---|---|
| Polar: | | |
| G | 25 | 8.17 |
| S | 18 | 5.88 |
| T | 11 | 3.59 |
| C | 4 | 1.31 |
| Y | 16 | 5.23 |
| N | 5 | 1.63 |
| Q | 11 | 3.59 |
| Acidic: | | |
| D | 26 | 8.50 |
| E | 24 | 7.84 |
| Basic: | | |
| K | 25 | 8.17 |
| R | 14 | 4.58 |
| H | 13 | 4.25 |

Example 2

Mouse Immunization Studies

Figure 7:
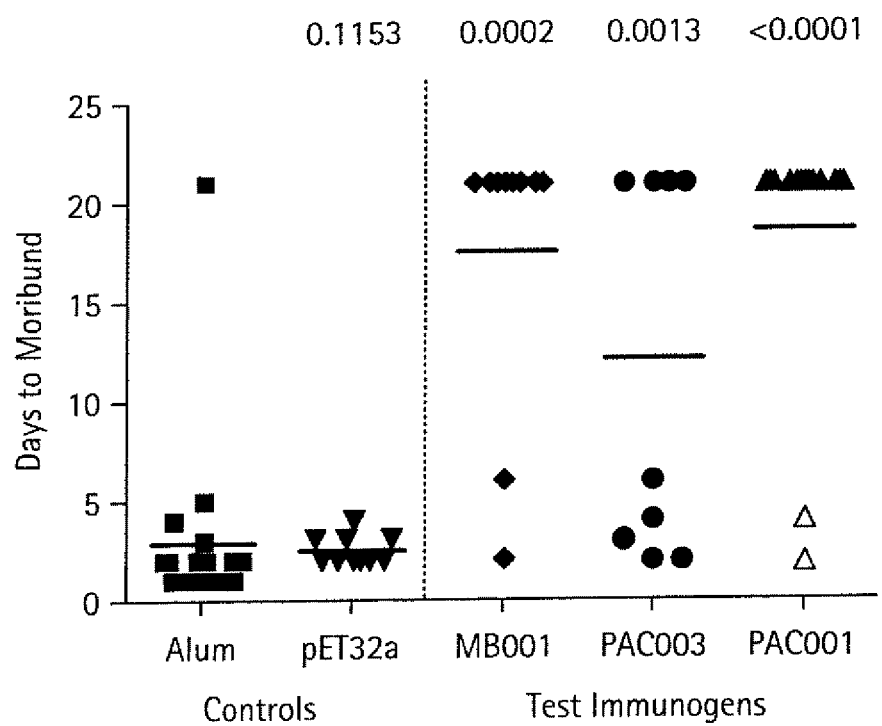
FIG. 7 presents data following immunization with proline-rich regions of PspA and challenge with capsular type 3 strain 3JYP2670.

The recombinant proteins PAC001, PAC003, and MB001 were used to immunize mice. MB001 contains SM-1 plus ½ of PAC001, including the non-pro block. Mice were immunized subcutaneously three times at ten-day intervals with alum as an adjuvant. Controls were immunized with alum alone, or with alum plus recombinant protein (fusion partner as a control that the process was not causing a non-specific immunity). The reason for using a fusion partner in this case is to facilitate purification and to be sure that the peptides were large enough to have adequate immunogenicity. Subsequently, the mice were challenged with a lethal dose of live *S. pneumoniae* 3JYP2670 delivered intravenously by tail vein injection. The challenge strain has a PspA that was non-cognate with any of the three recombinant proteins and thus tested for cross-protection. The times until the mice became moribund were recorded, as reflected in FIG. 4 and FIG. 7. For each of the three immunogens tested, protective responses were elicited as judged by increased survival times.

Figure 4:
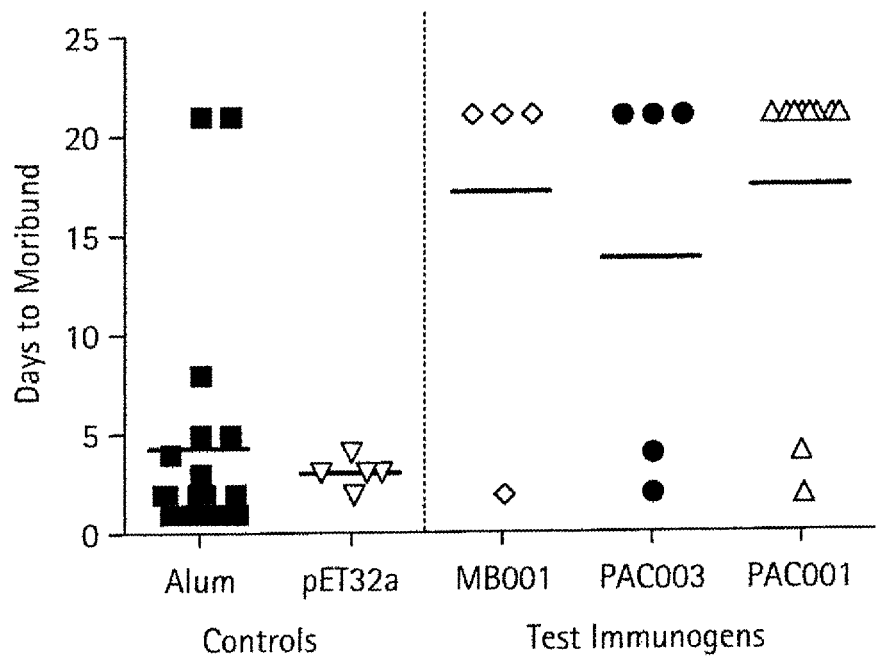
FIG. 4 is a graphical representation of results of the mouse sepsis challenge exemplified herein.

Referring to FIG. 4, the results for MB001 were different statistically from the alum control at P=0.021. The results for PAC001 were different statistically from the alum control at P=0.0006. For PAC003, the results were not quite significant (0.0537) from alum, but three of the five mice survived versus two of the fourteen for the alum control. The difference may become more significant if more mice are used. The results with the fusion partner were consistent with those obtained by alum, although the number of mice tested was much smaller. It was clear from this experiment that the proline-rich sequence of PspA can elicit protection.

The recombinant protein from pCD42_NPB (GST_NPB) was made to test whether this portion of the PspA and PspC peptides can elicit protective antibodies in animal model systems and in humans. If this activity is found, further studies will indicate how broad the protection is (i.e. can it protect against strains with different PspAs) Additionally, for example, whether antibodies can bind encapsulated cells, whether antibodies can increase complement deposition, and whether antibodies bind only growing cells are then investigated.

Because the proline-rich region, whether it contains a non-pro-block, is not part of the coiled-coil sequence, as predicted in FIGS. 5A-C, and should not elicit any antibody cross-reactive with epitopes in coiled-coil protein sequences including those in myosin.

Example 3

Antibody Binding Studies

Figure 8:
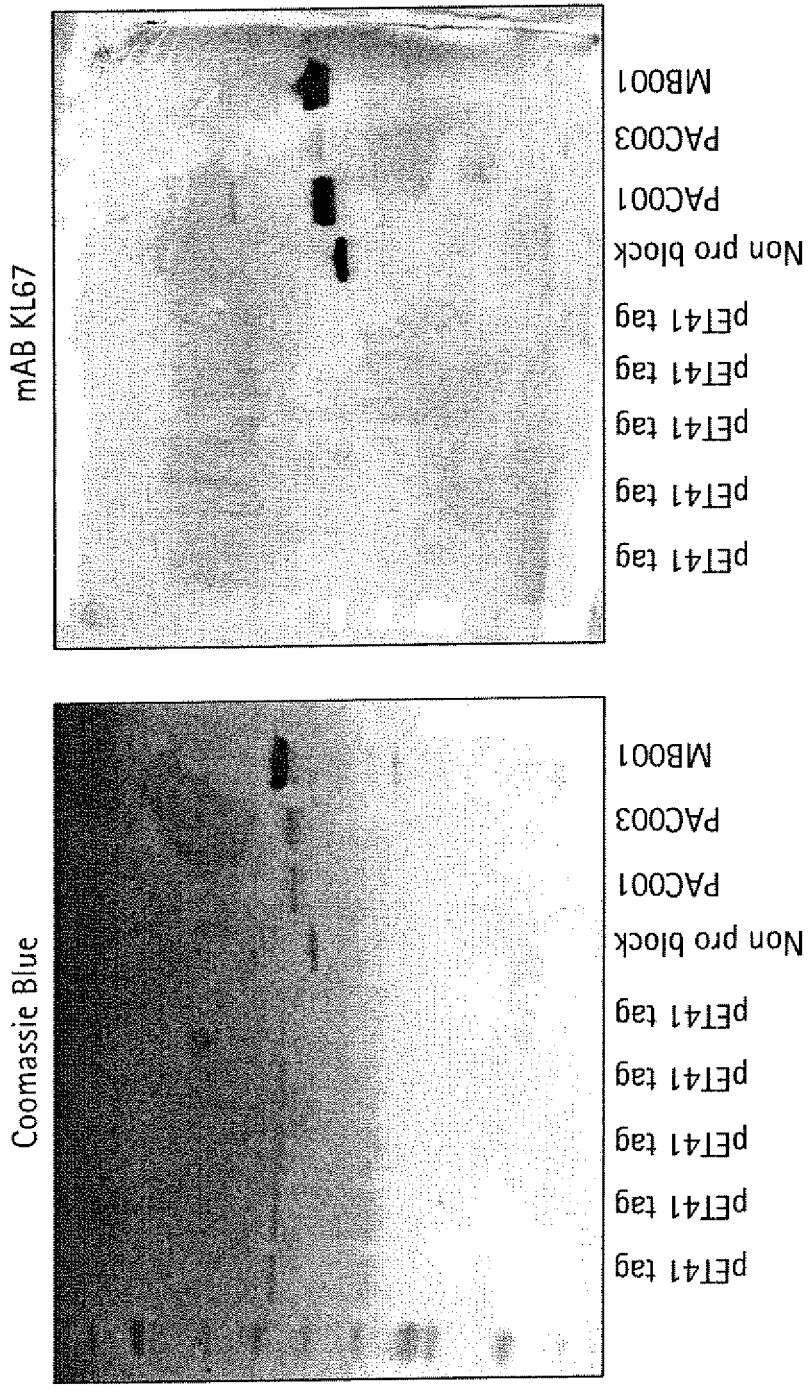
FIG. 8 shows a stained gel and corresponding Western blot indicating that mAb KL67 is specific to the non-proline-block of the proline-rich region of PspA/PspC polypeptides.

The monoclonal antibody designated KL67 was determined to bind specifically with the non-proline block of the proline-rich region embedded within some PspA and PspC proteins. Peptides of PspA and KL67 specificity are shown in the stained gel and corresponding Western blot depicted in FIG. 8.

The antibody binding of KL67 (anti-PspA-NPB) to *Streptococcus pneumoniae* strains, as detected by flow cytometry analysis using FITC-conjugated to mouse IgG, is depicted in FIG. 9. Antibody was diluted ⅓ and shown is the average of three experiments. Values on the vertical scale are "times greater than control", is the quotient of fluorescence of the labeled bacteria divided by the fluorescence of bacteria labelled with second antibody only. The strains are given in legend and include D39 wildtype strain and mutants that are lacking expression of PspA and PspC or capsule as indicated. The first three strains are encapsulated. In strain D39, both the PspA gene and the PspC gene have proline-rich regions that contain the NPB recognized by mAb KL67.

Figure 10:
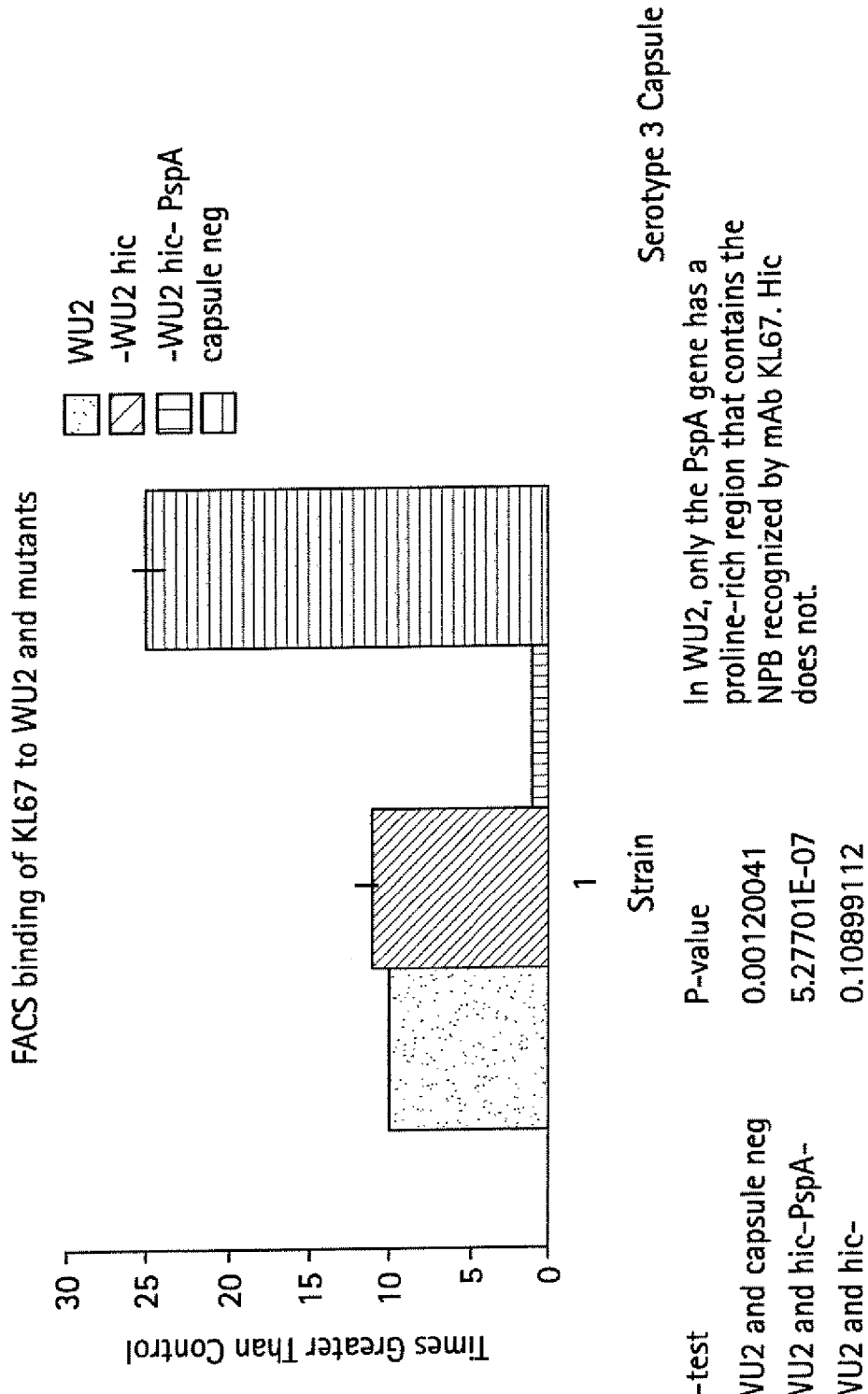
FIG. 10 presents data from FACS binding of mAb KL67 to WU2 wildtype strain and mutant strains that lack PspA and Hic, or capsule.

Another study of the antibody binding of KL67 to *Streptococcus pneumoniae* strains, as detected by flow cytometry analysis using FITC-conjugated to mouse IgG, is summarized in FIG. 10. Antibody was diluted ⅓ and shown is the average of three experiments. Values on the vertical scale are "times greater than control", is the quotient of fluorescence of the labeled bacteria divided by the fluorescence of bacteria labelled with second antibody only. The strains are given in legend and include WU2 wildtype strain and WU2 mutants that are lacking expression of PspA and Hic or capsule as indicated. The first three strains are encapsulated. In the WU2 strain, only the PspA gene has a proline-rich region that contains the NPB recognized by KL67. Hic does not.

An additional study on the binding of KL67 pneumococcal strains, as detected by flow cytometry analysis using FITC-conjugated to mouse IgG, is summarized in FIG. 11. Antibody was diluted ⅓ and shown is the average of three experiments. Values on the vertical scale are "times greater than control", is the quotient of fluorescence of the labeled bacteria divided by the fluorescence of bacteria labelled with second antibody only. The strains are given in legend and include TIGR4 wildtype strain and mutants that are lacking expression of PspA, PspC, both or capsule as indicated. The first five strains are encapsulated. In strain TIGR4, only the PspC gene has a proline-rich region that contains the NPB recognized by mAb KL67. PspA does not.

These studies indicate that mAb KL67 recognized specifically the NPB region present in proline-rich regions of some PspA and PspC molecules. The NPB in either the PspA or PspC context is accessible to mAb KL67 antibody on live *S. pneumoniae* with capsule 2, capsule 3, and capsule 4 serotypes. Additionally, the NBP on PspA is slightly more accessible to antibody in absence of PspC and in the absence of capsule. Also, polyclonal sera raised against the construct PAC001 binds the surface of pneumococcal cells.

The invention claimed is:

1. An immunogenic composition comprising a pharmaceutically acceptable carrier or an adjuvant and at least one purified, immunogenic, recombinant polypeptide of *Streptococcus pneumoniae* surface protein A (PspA) consisting of SEQ. ID, NO:1, SEQ ID NO: 2, SEQ ID NO: 4, SEQ ID NO:6, SEQ ID NO:7, SEQ ID NO:45, amino acid residues 159-267 of SEQ ID NO:20, or amino acid residues 159-263 of SEQ ID NO:18; wherein said polypeptide lacks an alpha-helical region of the full length PspA; and wherein said polypeptide is immunogenic against *S. pneumoniae*.

2. A vaccine comprising the immunogenic composition of claim 1.

3. The vaccine of claim 2, in which said composition comprises at least one polypeptide consisting of SEQ. ID, NO: 1, SEQ ID NO: 2, SEQ ID NO: 4 or amino acid residues 159-263 of SEQ ID NO: 18.

4. An immunogenic composition comprising a pharmaceutically acceptable carrier or an adjuvant and at least one purified, recombinant protein consisting of amino acid residues 159-263 of SEQ ID NO: 18; wherein the polypeptide lacks an alpha-helical region of the full length PspA; and wherein the composition is immunogenic against *S. pneumoniae*.

5. A vaccine comprising the immunogenic composition of claim 4.

* * * * *